(12) United States Patent
Khakoo

(10) Patent No.: US 10,995,116 B2
(45) Date of Patent: May 4, 2021

(54) PEPTIDE-INDUCED NK CELL ACTIVATION

(71) Applicant: University of Southampton, Southampton (GB)

(72) Inventor: Salim Iqbal Khakoo, Southampton (GB)

(73) Assignee: University of Southampton

(*) Notice: Subject to any disclaimer, the term of this patent is extended or adjusted under 35 U.S.C. 154(b) by 446 days.

(21) Appl. No.: 15/310,014

(22) PCT Filed: May 8, 2015

(86) PCT No.: PCT/GB2015/051370
§ 371 (c)(1),
(2) Date: Nov. 9, 2016

(87) PCT Pub. No.: WO2015/170123
PCT Pub. Date: Nov. 12, 2015

(65) Prior Publication Data
US 2017/0137466 A1 May 18, 2017

(30) Foreign Application Priority Data

May 9, 2014 (GB) .................................. 1408264
Feb. 9, 2015 (GB) .................................. 1502122

(51) Int. Cl.
*C07K 7/06* (2006.01)
*C12N 5/0783* (2010.01)
*C07K 14/74* (2006.01)
*C12N 7/00* (2006.01)
*C12Q 1/6883* (2018.01)
*A61K 38/00* (2006.01)

(52) U.S. Cl.
CPC .......... *C07K 7/06* (2013.01); *C07K 14/70539* (2013.01); *C12N 5/0646* (2013.01); *C12N 7/00* (2013.01); *C12Q 1/6883* (2013.01); *A61K 38/00* (2013.01); *C07K 2319/70* (2013.01); *C12N 2501/998* (2013.01); *Y02A 50/30* (2018.01)

(58) Field of Classification Search
CPC ..................................................... C07K 7/06
See application file for complete search history.

(56) References Cited

U.S. PATENT DOCUMENTS

| 2006/0093617 A1 | 5/2006 | Buyse et al. |
| 2008/0249283 A1 | 10/2008 | Miyakawa et al. |

FOREIGN PATENT DOCUMENTS

| EP | 1652858 A1 | 5/2006 |
| EP | 1757687 A1 | 2/2007 |
| WO | WO-1999/058658 A2 | 11/1999 |
| WO | WO-2001/021189 A1 | 3/2001 |
| WO | WO-0121189 A1 * | 3/2001 | ........... C07K 14/005 |
| WO | WO-2003/040165 A2 | 5/2003 |
| WO | WO-2004/024182 A2 | 3/2004 |

OTHER PUBLICATIONS

Janeway et al. (Immunobiology: The Immune System in Health and Disease. 5th edition. New York: Garland Science; 2001) (Year: 2001).*
Khakoo et al. (2004, Science, vol. 305, pp. 872-874) (Year: 2004).*
Davidson et al. (1985, JBC, vol. 260(25), pp. 13414-13423). (Year: 1985).*
Blais et al., 2011, Immunology, vol. 133, pp. 1-7 (Year: 2011).*
Alter et al., (2009), "HLA class I subtype-dependent expansion of KIR3DS1+ and KIR3DL1+ NK cells during acute human immunodeficiency virus type 1 infection," *J. Virol.*, 83(13):6798-805.
Alter et al., (2010), "Reduced frequencies of NKp30+NKp46+, CD161+ and NKG2D+ NK cells in acute HCV infection may predict viral clearance," *J. Hepatol.*, 55(2):278-88.
Andersen et al., (1999), "An assay for peptide binding to HLA-cw*0102," *Tissue Antigens*, 54(2):185-190.
Anton et al., (1997), "MHC class I-associated peptides produced from endogenous gene products with vastly different efficiencies," *J. Immunol.*, 158(6):2535-42.
Beziat et al., (2012), "CMV drives clonal expansion of NKG2C+ NK cells expressing self-specific KIRs in chronic hepatitis patients," *Eur. J. Immunol.*, 42(2):447-57.
Beziat et al., (2013), "NK cell responses to cytomegalovirus infection lead to stable imprints in the human KIR repertoire and involve activating KIRs," *Blood*, 121(14):2678-88.
Bjorkstrom et al., (2011), "Rapid expansion and long-term persistence of elevated NK cell numbers in humans infected with hantavirus," *J. Exp. Med.*, 208(1):13-21.
Borhis et al., (2013), "A Peptide Antagonist Disrupts NK Cell Inhibitory Synapse Formation," *J. Immunol.*, 190(6):2924-30.
Carrington et al., (2005), "Hierarchy of resistance to cervical neoplasia mediated by combinations of killer immunoglobulin-like receptor and human leukocyte antigen loci," *J. Exp. Med.*, 201(7):1069-75.
Cassidy et al., (2011), "Abstract No. 735: Natural killer cell response to hepatitis C peptides," Immunology, 135 (Suppl. 1):109, presented at the Annual Congress of the British Society for Immunology, Liverpool UK, on Dec. 5-8, 2011.
Cheent et al., (2013), "Synergistic inhibition of natural killer cells by the nonsignaling molecule CD94," *Proc. Natl. Acad. Sci. USA*, 110(42):16981-6.

(Continued)

*Primary Examiner* — Thaian N. Ton
*Assistant Examiner* — David A. Montanari
(74) *Attorney, Agent, or Firm* — Goodwin Procter LLP

(57) ABSTRACT

This invention relates to NK cell activation and NK cell mediated immunity, immunogenic peptides, compositions and complexes; and associated methods of treatment or prophylaxis. In particular, a peptide capable of activating NK cell-mediated immunity, the peptide comprising or consisting of the amino acid sequence $X''AX^2X^1$ wherein $X''$ is an amino acid sequence of between 5 and 12 residues, and $X^1$ is any amino acid; or leucine or isoleucine; and $X_2$ is alanine, threonine, tryptophan, or serine.

12 Claims, 9 Drawing Sheets

Figure 1:
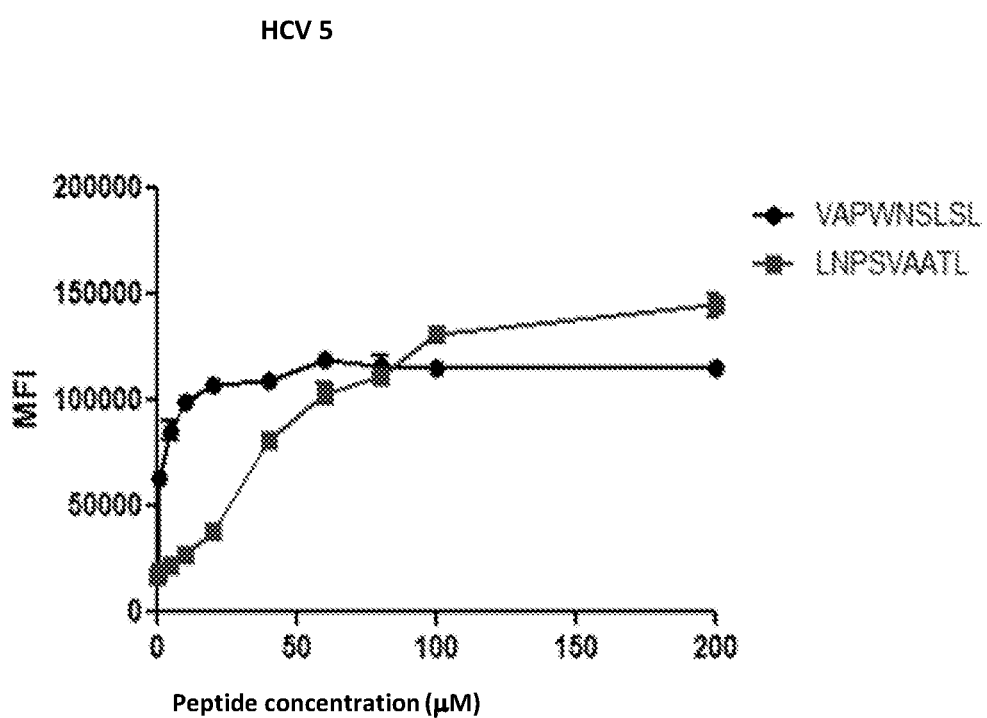

Specification includes a Sequence Listing.

(56) References Cited

OTHER PUBLICATIONS

Croft et al., (2013), "Kinetics of antigen expression and epitope presentation during virus infection," *PLoS Pathog.* 9(1):e1003129.
David et al., (2013), "Large spectrum of HLA-C recognition by killer Ig-like receptor (KIR)2DL2 and KIR2DL3 and restricted C1 specificty of KIR2DS2: dominant impact of KIR2DL2/KIR2DS2 on KIR2D NK cell repertoire formation," *J. Immunol.*, 191(9):4778-88.
Deshpande et al., (2008), "Variation in HLA class I antigen-processing genes and susceptibility to human papillomavirus type 16-associated cervical cancer," *J. Infect. Dis.*, 197(3):371-81.
Fadda et al. (2010), "Peptide antagonism as a mechanism for NK cell activation," *Proc. Natl. Acad. Sci. USA*,107(22):10160-5.
Fadda et al., (2012), "HLA-cw*0102-Restricted HIV-1 p24 Epitope Variants Can Modulate the Binding of the Inhbitory KIR2DL2 Receptor and Primary NK Cell Function," 8(7):e1002805.
Gatfield et al., (1998), "Cell lines transfected with the TAP inhibitor ICP47 allow testing peptide binding to a variety of HLA class I molecules," *Int. Immunol.*, 10(11):1665-72.
Harrison et al., (2010), "Association of NKG2A with treatment for chronic hepatitis C virus infection," *Clin. Exp. Immunol.*, 161(2):306-14.
Hiby et al., (2010), "Maternal activating KIRs protect against human reproductive failure mediated by fetal HLA-C2," *J. Clin. Invest.*, 120(11):4102-10.
Hirayasu et al., (2012), "Significant Association of KIR2DL3-HLA-C1 Combination with Cerebral Malaria and Implications for Co-evolution of KIR and HLA," *PLoS Pathog.*, 8(3):e1002565.
International Search Report for International Patent Application No. PCT/GB2015/051370 dated Dec. 11, 2015 (8 pages).
Khakoo et al., (2004), HLA and NK cell inhibitory receptor genes in resolving hepatitis C virus Infection, *Science*, 305(5685):872-4.
Khakoo, (2011), "Abstract No. 873: Natural killer cells and Hepatitis C virus infection," Immunology, 135(Suppl. 1):109, presented at the Annual Congress of the British Society for Immunology, Liverpool UK, on Dec. 5-8, 2011.
Knapp et al., (2010), "Consistent beneficial effects of killer cell immunoglobulin-like receptor 2DL3 and group 1 human leukocyte antigen-C following exposure to hepatitis C virus," *Hepatology*, 51(4):1168-75.
Koerner et al., (2012), "HLA-cw*0102-restricted HIV-1 p24 epitope variants can modulate the binding of the inhibitory KIR2DL2 receptor and primary NK cell function," *Retrovirology.* 9(Suppl 2):P177.
Korner et al., (2012), "Role of KIR3DS1 in human diseases," *Front. Immunol.*, 3:326.
Liberatore et al., (1999), "Natural killer cell-mediated lysis of autologous cells modified by gene therapy," *J. Exp. Med.*, 189(12):1855-62.
Lopez-Vazquez et al., (2005), "Protective Effect of the HLA-Bw4I80 Epitope and the Killer Cell Immunoglobulin-Like Receptor 3DS1 Gene against the Development of Hepatocellular Carcinoma in Patients with Hepatitis C Virus Infection," *J. Infect. Dis.*, 2 192(1):162-5.
Malnati et al., (1995), "Peptide specificity in the recognition of MHC class I by natural killer cell clones," *Science*, 267(5200):1016-8.
Marcus et al., (2013), "Evidence for natural killer cell memory," *Curr. Biol.*, 23(17):R817-20.
Martin et al., (2002), "Epistatic interaction between KIR3DS1 and HLA-B delays the progression to AIDS," *Nat. Genet.*, 31(4):429-34.
Minskaia, (2013), "Protein coexpression using FMDV 2A: effect of 'linker' residues," *BioMed Res, Int.*, 2013:291730.
Moesta et al., (2012), "Diverse functionality among human NK cell receptors for the C1 epitope of HLA-C: KIR2DS2, KIR2DL2, and KIR2DL3," *Front. Immunol.*, 3:336.
Mottez et al., (1995), "Cells Expressin a Major Histocompatibility Complex Class I Molecule with a Single Covalently Bound Peptide are Highly Immunogenic," *J. Exp. Med.*, 181:493-502.
Pan et al., (2011), "KIR and HLA loci are associated with hepatocellular carcinoma development in patients with hepatitis B virus infection: a case-control study," *PLoS ONE*, 6(10):e25682.
Paust et al., (2011), "Natural killer cell memory," *Nat. Immunol.*, 131(6):500-8.
Peng et al., (2013), "Liver-resident NK cells confer adaptive immunity in skin-contact inflammation," *J. Clin. Invest.*, 123(4):1444-56.
Petitdemange et al., (2011), "Unconventional repertoire profile is imprinted during acute chikungunya infection for natural killer cells polarization toward cytotoxicity," *PLoS Pathog.*, 7(9):e1002268.
Rammensee et al., (1999), "SYFPEITHI: database for MHC ligands and peptide motifs," *Immunogenetics*, 50(3-4):213-9.
Seidel et al., (2013), "Microscale thermophoresis quantifies biomolecular interactions under previously challenging conditions," *Methods*, 59(3):301-15.
Stewart et al., (2005), "Recognition of peptide-MHC class I complexes by activating killer immunoglobulin-like receptors," *Proc. Natl. Acad. Sci. USA*, 102(37):13224-9.
Sun et al., (2009), "Adaptive immune features of natural killer cells," *Nature*, 457(7229):557-61.
Suppiah et al., (2011), "IL28B, HLA-C, and KIR variants additively predict response to therapy in chronic hepatitis C virus infection in a European Cohort: a cross-sectional study," *PLoS Med.*, 8(9):e1001092.
Tomasello et al., (1998), "Gene structure, expression pattern, and biological activity of mouse killer cell activating receptor-associated protein (KARAP)/DAP-12," *J. Biol. Chem.*, 273(51):34115-9.
UK Intellectual Property Office Search Report Issued in Application No. GB+1408264.8 dated Feb. 16, 2015 (6 pages).
Walshe et al., (2009), "Integrating In Silico and In Vitro Analysis of Peptide Binding Affinity to HLA-Cw*0102: A bioinformatic Approach to the Prediction of New Epitopes," PLoS One, 4(11):e8095.
Wienken et al., (2010), "Protein-binding assays in biological liquids using microscale thermophoresis," *Nat. Commun.*, 1:100.
Written Opinion of the International Searching Authority (ISA/EP) for International Patent Application No. PCT/GB2015/051370 dated Dec. 11, 2015 (10 pages).

* cited by examiner

SEQUENCE LISTING

```
<160> NUMBER OF SEQ ID NOS: 51

<210> SEQ ID NO 1
<211> LENGTH: 9
<212> TYPE: PRT
<213> ORGANISM: Homo sapiens
```

```
<400> SEQUENCE: 1

Leu Asn Pro Ser Val Ala Ala Thr Leu
1               5

<210> SEQ ID NO 2
<211> LENGTH: 8
<212> TYPE: PRT
<213> ORGANISM: Homo sapiens

<400> SEQUENCE: 2

Asn Pro Ser Val Ala Ala Thr Leu
1               5

<210> SEQ ID NO 3
<211> LENGTH: 7
<212> TYPE: PRT
<213> ORGANISM: Homo sapiens

<400> SEQUENCE: 3

Pro Ser Val Ala Ala Thr Leu
1               5

<210> SEQ ID NO 4
<211> LENGTH: 9
<212> TYPE: PRT
<213> ORGANISM: Homo sapiens

<400> SEQUENCE: 4

Val Ala Pro Trp Asn Ala Ala Thr Leu
1               5

<210> SEQ ID NO 5
<211> LENGTH: 8
<212> TYPE: PRT
<213> ORGANISM: Homo sapiens

<400> SEQUENCE: 5

Ala Pro Trp Asn Ala Ala Thr Leu
1               5

<210> SEQ ID NO 6
<211> LENGTH: 7
<212> TYPE: PRT
<213> ORGANISM: Homo sapiens

<400> SEQUENCE: 6

Pro Trp Asn Ala Ala Thr Leu
1               5

<210> SEQ ID NO 7
<211> LENGTH: 9
<212> TYPE: PRT
<213> ORGANISM: Homo sapiens

<400> SEQUENCE: 7

Val Ala Pro Trp Asn Ser Ala Thr Leu
1               5

<210> SEQ ID NO 8
<211> LENGTH: 8
<212> TYPE: PRT
<213> ORGANISM: Homo sapiens

<400> SEQUENCE: 8
```

Ala Pro Trp Asn Ser Ala Thr Leu
1               5

<210> SEQ ID NO 9
<211> LENGTH: 7
<212> TYPE: PRT
<213> ORGANISM: Homo sapiens

<400> SEQUENCE: 9

Pro Trp Asn Ser Ala Thr Leu
1               5

<210> SEQ ID NO 10
<211> LENGTH: 9
<212> TYPE: PRT
<213> ORGANISM: Homo sapiens

<400> SEQUENCE: 10

Val Ala Pro Trp Asn Ser Ala Ala Leu
1               5

<210> SEQ ID NO 11
<211> LENGTH: 8
<212> TYPE: PRT
<213> ORGANISM: Homo sapiens

<400> SEQUENCE: 11

Ala Pro Trp Asn Ser Ala Ala Leu
1               5

<210> SEQ ID NO 12
<211> LENGTH: 7
<212> TYPE: PRT
<213> ORGANISM: Homo sapiens

<400> SEQUENCE: 12

Pro Trp Asn Ser Ala Ala Leu
1               5

<210> SEQ ID NO 13
<211> LENGTH: 9
<212> TYPE: PRT
<213> ORGANISM: Homo sapiens

<400> SEQUENCE: 13

Val Ala Pro Trp Asn Ala Ala Ala Leu
1               5

<210> SEQ ID NO 14
<211> LENGTH: 8
<212> TYPE: PRT
<213> ORGANISM: Homo sapiens

<400> SEQUENCE: 14

Ala Pro Trp Asn Ala Ala Ala Leu
1               5

<210> SEQ ID NO 15
<211> LENGTH: 9
<212> TYPE: PRT
<213> ORGANISM: Homo sapiens

<400> SEQUENCE: 15

Gly Ala Val Pro Asp Leu Ala Trp Leu
1               5

```
<210> SEQ ID NO 16
<211> LENGTH: 9
<212> TYPE: PRT
<213> ORGANISM: Homo sapiens

<400> SEQUENCE: 16

Gly Ala Val Pro Asp Leu Ala Thr Leu
1               5

<210> SEQ ID NO 17
<211> LENGTH: 7
<212> TYPE: PRT
<213> ORGANISM: Homo sapiens

<400> SEQUENCE: 17

Pro Trp Asn Ala Ala Ala Leu
1               5

<210> SEQ ID NO 18
<211> LENGTH: 9
<212> TYPE: PRT
<213> ORGANISM: Homo sapiens

<400> SEQUENCE: 18

Leu Asn Pro Ser Val Ala Ala Thr Ile
1               5

<210> SEQ ID NO 19
<211> LENGTH: 8
<212> TYPE: PRT
<213> ORGANISM: Homo sapiens

<400> SEQUENCE: 19

Asn Pro Ser Val Ala Ala Thr Ile
1               5

<210> SEQ ID NO 20
<211> LENGTH: 7
<212> TYPE: PRT
<213> ORGANISM: Homo sapiens

<400> SEQUENCE: 20

Pro Ser Val Ala Ala Thr Ile
1               5

<210> SEQ ID NO 21
<211> LENGTH: 9
<212> TYPE: PRT
<213> ORGANISM: Homo sapiens

<400> SEQUENCE: 21

Val Ala Pro Trp Asn Ala Ala Thr Ile
1               5

<210> SEQ ID NO 22
<211> LENGTH: 8
<212> TYPE: PRT
<213> ORGANISM: Homo sapiens

<400> SEQUENCE: 22

Ala Pro Trp Asn Ala Ala Thr Ile
1               5
```

```
<210> SEQ ID NO 23
<211> LENGTH: 7
<212> TYPE: PRT
<213> ORGANISM: Homo sapiens

<400> SEQUENCE: 23

Pro Trp Asn Ala Ala Thr Ile
1               5

<210> SEQ ID NO 24
<211> LENGTH: 9
<212> TYPE: PRT
<213> ORGANISM: Homo sapiens

<400> SEQUENCE: 24

Val Ala Pro Trp Asn Ser Ala Thr Ile
1               5

<210> SEQ ID NO 25
<211> LENGTH: 8
<212> TYPE: PRT
<213> ORGANISM: Homo sapiens

<400> SEQUENCE: 25

Ala Pro Trp Asn Ser Ala Thr Ile
1               5

<210> SEQ ID NO 26
<211> LENGTH: 7
<212> TYPE: PRT
<213> ORGANISM: Homo sapiens

<400> SEQUENCE: 26

Pro Trp Asn Ser Ala Thr Ile
1               5

<210> SEQ ID NO 27
<211> LENGTH: 9
<212> TYPE: PRT
<213> ORGANISM: Homo sapiens

<400> SEQUENCE: 27

Val Ala Pro Trp Asn Ser Ala Ala Ile
1               5

<210> SEQ ID NO 28
<211> LENGTH: 8
<212> TYPE: PRT
<213> ORGANISM: Homo sapiens

<400> SEQUENCE: 28

Ala Pro Trp Asn Ser Ala Ala Ile
1               5

<210> SEQ ID NO 29
<211> LENGTH: 7
<212> TYPE: PRT
<213> ORGANISM: Homo sapiens

<400> SEQUENCE: 29

Pro Trp Asn Ser Ala Ala Ile
1               5

<210> SEQ ID NO 30
<211> LENGTH: 9
```

```
<212> TYPE: PRT
<213> ORGANISM: Homo sapiens

<400> SEQUENCE: 30

Leu Asn Pro Ser Val Ala Ala Ala Leu
1               5

<210> SEQ ID NO 31
<211> LENGTH: 8
<212> TYPE: PRT
<213> ORGANISM: Homo sapiens

<400> SEQUENCE: 31

Asn Pro Ser Val Ala Ala Ala Leu
1               5

<210> SEQ ID NO 32
<211> LENGTH: 7
<212> TYPE: PRT
<213> ORGANISM: Homo sapiens

<400> SEQUENCE: 32

Pro Ser Val Ala Ala Ala Leu
1               5

<210> SEQ ID NO 33
<211> LENGTH: 9
<212> TYPE: PRT
<213> ORGANISM: Homo sapiens

<400> SEQUENCE: 33

Leu Asn Pro Ser Val Ala Ala Ser Leu
1               5

<210> SEQ ID NO 34
<211> LENGTH: 8
<212> TYPE: PRT
<213> ORGANISM: Homo sapiens

<400> SEQUENCE: 34

Asn Pro Ser Val Ala Ala Ser Leu
1               5

<210> SEQ ID NO 35
<211> LENGTH: 7
<212> TYPE: PRT
<213> ORGANISM: Homo sapiens

<400> SEQUENCE: 35

Pro Ser Val Ala Ala Ser Leu
1               5

<210> SEQ ID NO 36
<211> LENGTH: 9
<212> TYPE: PRT
<213> ORGANISM: Homo sapiens

<400> SEQUENCE: 36

Leu Asn Pro Ser Val Ala Ala Trp Leu
1               5

<210> SEQ ID NO 37
<211> LENGTH: 9
<212> TYPE: PRT
<213> ORGANISM: Homo sapiens
```

<400> SEQUENCE: 37

Leu Asn Pro Ser Val Ala Ala Trp Leu
1               5

<210> SEQ ID NO 38
<211> LENGTH: 7
<212> TYPE: PRT
<213> ORGANISM: Homo sapiens

<400> SEQUENCE: 38

Pro Ser Val Ala Ala Trp Leu
1               5

<210> SEQ ID NO 39
<211> LENGTH: 9
<212> TYPE: PRT
<213> ORGANISM: Homo sapiens

<400> SEQUENCE: 39

Leu Asn Pro Ser Val Ala Ala Ala Ile
1               5

<210> SEQ ID NO 40
<211> LENGTH: 8
<212> TYPE: PRT
<213> ORGANISM: Homo sapiens

<400> SEQUENCE: 40

Asn Pro Ser Val Ala Ala Ala Ile
1               5

<210> SEQ ID NO 41
<211> LENGTH: 7
<212> TYPE: PRT
<213> ORGANISM: Homo sapiens

<400> SEQUENCE: 41

Pro Ser Val Ala Ala Ala Ile
1               5

<210> SEQ ID NO 42
<211> LENGTH: 9
<212> TYPE: PRT
<213> ORGANISM: Homo sapiens

<400> SEQUENCE: 42

Leu Asn Pro Ser Val Ala Ala Ser Ile
1               5

<210> SEQ ID NO 43
<211> LENGTH: 8
<212> TYPE: PRT
<213> ORGANISM: Homo sapiens

<400> SEQUENCE: 43

Asn Pro Ser Val Ala Ala Ser Ile
1               5

<210> SEQ ID NO 44
<211> LENGTH: 7
<212> TYPE: PRT
<213> ORGANISM: Homo sapiens

<400> SEQUENCE: 44

```
Pro Ser Val Ala Ala Ser Ile
1               5

<210> SEQ ID NO 45
<211> LENGTH: 9
<212> TYPE: PRT
<213> ORGANISM: Homo sapiens

<400> SEQUENCE: 45

Leu Asn Pro Ser Val Ala Ala Trp Ile
1               5

<210> SEQ ID NO 46
<211> LENGTH: 8
<212> TYPE: PRT
<213> ORGANISM: Homo sapiens

<400> SEQUENCE: 46

Asn Pro Ser Val Ala Ala Trp Ile
1               5

<210> SEQ ID NO 47
<211> LENGTH: 7
<212> TYPE: PRT
<213> ORGANISM: Homo sapiens

<400> SEQUENCE: 47

Pro Ser Val Ala Ala Trp Ile
1               5

<210> SEQ ID NO 48
<211> LENGTH: 9
<212> TYPE: PRT
<213> ORGANISM: Homo sapiens

<400> SEQUENCE: 48

Val Ala Pro Trp Asn Ser Leu Ser Leu
1               5

<210> SEQ ID NO 49
<211> LENGTH: 9
<212> TYPE: PRT
<213> ORGANISM: Homo sapiens

<400> SEQUENCE: 49

Val Ala Pro Trp Asn Ser Phe Ala Leu
1               5

<210> SEQ ID NO 50
<211> LENGTH: 8
<212> TYPE: PRT
<213> ORGANISM: Homo sapiens
<220> FEATURE:
<221> NAME/KEY: misc_feature
<222> LOCATION: (1)..(5)
<223> OTHER INFORMATION: Xaa can be any naturally occurring amino acid

<400> SEQUENCE: 50

Xaa Xaa Xaa Xaa Xaa Ala Ala Leu
1               5

<210> SEQ ID NO 51
<211> LENGTH: 8
<212> TYPE: PRT
<213> ORGANISM: Homo sapiens
```

```
<220> FEATURE:
<221> NAME/KEY: misc_feature
<222> LOCATION: (1)..(5)
<223> OTHER INFORMATION: Xaa can be any naturally occurring amino acid

<400> SEQUENCE: 51

Xaa Xaa Xaa Xaa Xaa Ala Thr Leu
1               5
```

PEPTIDE-INDUCED NK CELL ACTIVATION

This application is a 371 National Stage Application of PCT/GB2015/051370, filed May 8, 2015, which claims the benefit of and priority to United Kingdom Patent Application No. 1502122.3, filed Feb. 9, 2015 and United Kingdom Patent Application No. 1408264.8, filed May 9, 2014.

This invention relates to NK cell activation and NK cell mediated immunity, immunogenic peptides, compositions and complexes; and associated methods of treatment or prophylaxis.

Natural killer (NK) cells are important in the immune response to cancer, inflammatory disorders and globally important infections, such as HIV, hepatitis B (HBV), hepatitis C (HCV), and malaria. Killer-cell immunoglobulin-like receptors (KIR) are expressed on NK cells and specific combinations of KIR and their HLA class I ligands lead to protection or susceptibility to HCV, HIV, HPV and malaria; to virus related cancers including hepatocellular carcinoma (HBV and HCV) and cervical cancer (HPV); to pregnancy associated disorders and the outcome of haematological malignancies and bone marrow transplantation[1-9].

Virus-specific long-lived "memory" NK cells have been demonstrated in mice[10-12]. Consistent with such populations in humans, expansions of NK cells expressing inhibitory or activating KIR specific for self-MHC class I have been observed in a number of viral infections (HCV, HIV, CMV, hantavirus) and associated with protection in both HCV and Chikungunya virus infection[13-17]. The drivers for these self-MHC class I specific expansions are not clear. However, KIR engage MHC class I and its bound peptide[18] and an unexpected sensitivity of NK cells to changes in the peptide content of MHC class I has been demonstrated[19, 20].

The specificity of inhibitory receptors has been well defined. Due to the high sequence homology in the ligand binding domains with related inhibitory receptors, ligands for the activating KIR have been considered to be similar to those of the inhibitory KIR, but generally of lower affinity. Thus, in general activating KIR are thought to engage MHC class I molecules and its bound peptide with the same motifs as their inhibitory counterparts.

An aim of the present invention is to provide an improved or alternative NK cell mediated therapy or prophylaxis.

According to a first aspect of the invention, there is provided a peptide capable of activating NK cell-mediated immunity, the peptide comprising or consisting of the amino acid sequence $X''AX^2X^1$,
wherein
$X''$ is an amino acid sequence of between 5 and 12 residues, and
$X^1$ is any amino acid; or leucine or isoleucine; and
$X^2$ is alanine, threonine, tryptophan, or serine.

In one embodiment $X^1$ is leucine or isoleucine. In one embodiment $X^1$ is leucine. Alternatively, in one embodiment $X^1$ is isoleucine.

In one embodiment $X^2$ is alanine or threonine. In another embodiment $X^2$ is tryptophan or threonine. In another embodiment $X^2$ is alanine. In another embodiment $X^2$ is threonine. In another embodiment $X^2$ is tryptophan. In one embodiment $X^1$ is leucine and $X^2$ is alanine or threonine. In another embodiment $X^1$ is leucine and $X^2$ is tryptophan or threonine. In another embodiment $X^1$ is leucine and $X^2$ is tryptophan. In another embodiment $X^1$ is leucine and $X^2$ is threonine. In another embodiment $X^1$ is leucine and $X^2$ is alanine.

$X''$ may be an amino acid sequence of 5 residues. $X''$ may be an amino acid sequence of 6 residues. $X''$ may be an amino acid sequence of 7 residues. $X''$ may be an amino acid sequence of 5 residues and $X^1$ is leucine. $X''$ may be an amino acid sequence of 6 residues and $X^1$ is leucine. $X''$ may be an amino acid sequence of 7 residues and $X^1$ is leucine. $X''$ may be an amino acid sequence of 7 residues and $X^2$ is tryptophan. $X''$ may be an amino acid sequence of 7 residues and $X^2$ is threonine.

The peptide amino acid sequence may comprise any sequence selected from the group comprising:

LNPSVAATL; (SEQ ID NO: 1)

NPSVAATL; (SEQ ID NO: 2)

PSVAATL; (SEQ ID NO: 3)

VAPWNAATL; (SEQ ID NO: 4)

APWNAATL; (SEQ ID NO: 5)

PWNAATL; (SEQ ID NO: 6)

VAPWNSATL; (SEQ ID NO: 7)

APWNSATL; (SEQ ID NO: 8)

PWNSATL; (SEQ ID NO: 9)

VAPWNSAAL; (SEQ ID NO: 10)

APWNSAAL; (SEQ ID NO: 11)

PWNSAAL; (SEQ ID NO: 12)

VAPWNAAAL; (SEQ ID NO: 13)

APWNAAAL; (SEQ ID NO: 14)

GAVPDLAWL; (SEQ ID NO: 15)

GAVPDLATL and (SEQ ID NO: 16)

PWNAAAL. (SEQ ID NO: 17)

In an alternative embodiment, the peptide amino acid sequence may comprise any sequence selected from the group comprising:

LNPSVAATI; (SEQ ID NO: 18)

NPSVAATI; (SEQ ID NO: 19)

PSVAATI; (SEQ ID NO: 20)

VAPWNAATI; (SEQ ID NO: 21)

-continued

APWNAATI; (SEQ ID NO: 22)

PWNAATI; (SEQ ID NO: 23)

VAPWNSATI; (SEQ ID NO: 24)

APWNSATI; (SEQ ID NO: 25)

PWNSATI; (SEQ ID NO: 26)

VAPWNSAAI; (SEQ ID NO: 27)

APWNSAAI; (SEQ ID NO: 28)

PWNSAAI. (SEQ ID NO: 29)

The peptide amino acid sequence may comprise any sequence selected from the group comprising:

LNPSVAATL; (SEQ ID NO: 1)

NPSVAATL; (SEQ ID NO: 2)

PSVAATL; (SEQ ID NO: 3)

LNPSVAAAL; (SEQ ID NO: 30)

NPSVAAAL; (SEQ ID NO: 31)

PSVAAAL; (SEQ ID NO: 32)

LNPSVAASL; (SEQ ID NO: 33)

NPSVAASL; (SEQ ID NO: 34)

PSVAASL; (SEQ ID NO: 35)

LNPSVAAWL; (SEQ ID NO: 36)

NPSVAAWL; and (SEQ ID NO: 37)

PSVAAWL. (SEQ ID NO: 38)

The peptide amino acid sequence may comprise any sequence selected from the group comprising:

LNPSVAATI; (SEQ ID NO: 18)

NPSVAATI; (SEQ ID NO: 19)

PSVAATI; (SEQ ID NO: 20)

LNPSVAAAI; (SEQ ID NO: 39)

NPSVAAAI; (SEQ ID NO: 40)

PSVAAAI; (SEQ ID NO: 41)

LNPSVAASI; (SEQ ID NO: 42)

NPSVAASI; (SEQ ID NO: 43)

PSVAASI; (SEQ ID NO: 44)

LNPSVAAWI; (SEQ ID NO: 45)

NPSVAAWI; and (SEQ ID NO: 46)

PSVAAWI. (SEQ ID NO: 47)

The peptide amino acid sequence may comprise any sequence selected from the group comprising LNPSVAATL (SEQ ID NO: 1); LNPSVAAAL (SEQ ID NO: 30); LNPSVAASL (SEQ ID NO: 33); and LNPSVAAWL (SEQ ID NO: 36).

The peptide may comprise or consist of the amino acid sequence LNPSVAATL (SEQ ID NO: 1). In another embodiment the peptide may comprise or consist of the amino acid sequence VAPWNAATL (SEQ ID NO: 4). In another embodiment the peptide may comprise or consist of the amino acid sequence VAPWNSATL (SEQ ID NO: 7). In another embodiment the peptide may comprise or consist of the amino acid sequence VAPWNAAAL (SEQ ID NO: 13).

The peptide may comprise or consist of the amino acid sequence GAVPDLAWL (SEQ ID NO: 15). The peptide may comprise or consist of the amino acid sequence GAVPDLATL (SEQ ID NO: 16).

The peptide may be between about 8 and about 12 amino acid residues in length. The peptide may be between about 8 and about 15 amino acid residues in length. The peptide may be at least 8 amino acid residues in length. The peptide may be 9 amino acid residues in length.

The peptide may be an isolated peptide. The peptide may be immunogenic. The peptide may comprise a viral derived peptide, for example a peptide comprising or consisting of an amino acid sequence of a virus peptide or protein. The peptide may comprise an oncogenic peptide. The oncogenic peptide may be a peptide that is presented abnormally on a cell, such that it identifies the cell as cancerous. The peptide may be a self-peptide, that is, a peptide comprising a sequence that is encoded by a patient's genome. For example, a self-peptide may be encoded by a gene that is upregulated during infection.

The invention advantageously provides that MHC class I specific peptides can be utilized to drive activation and expansion of NK cells expressing specific inhibitory or activating KIR and that this property can be exploited to generate peptide specific protocols for NK cell therapy. This is attractive for NK cells because KIR have broad peptide: HLA specificities such that the immunogen and the antigen need not be the same. To date NK cell therapy is focused on generating large numbers of non-specific NK cells. However, understanding the concepts of the present invention would lead to peptide-specific activation of NK cells which would inform NK-based vaccination strategies and peptide-based protocols for generating specific sub-populations of NK cells that can be used therapeutically. In particular, activating KIR are associated with haematological malignancies. They have similar MHC class I:peptide specificities as the inhibitory KIR, but bind at much lower affinity[22-24]. Hence inhibition dominates over activation. In an embodiment, the invention identifies an HCV-derived peptide that specifically binds KIR2DS2, but not KIR2DL2. This means that KIR2DS2-positive NK cells could be activated by specific peptides.

According to another aspect of the invention, there is provided a complex comprising an MHC class I molecule and the peptide according to the invention. The MHC class I molecule may comprise an MHC class I truncated at the stem region of the α3 domain. The MHC class I molecule may comprise HLA-C, or part thereof. The HLA-C may be a group 1 HLA-C (e.g. HLA-C with lysine at residue 80 of the alpha helix of the MHC class I heavy chain). The MHC class I molecule may comprise HLA-Cw*0102. The MHC class I molecule may comprise HLA-C*0304. The complex may comprise a fusion protein of the MHC class I molecule and the peptide according to the invention. The complex may comprise a fusion protein of the MHC class I molecule HLA-Cw*0102 and the peptide according to the invention. The complex may comprise a fusion protein of the MHC class I molecule HLA-C*0304 and the peptide according to the invention. The complex may be an isolated complex.

According to another aspect of the invention, there is provided a vesicle comprising the complex of the invention.

The vesicle may be an exosome. The vesicle may be isolated. The exosome may be isolated from a cell arranged to express an MHC class I molecule, or part thereof, and the peptide according to the invention. The exosome may be isolated from a cell arranged to express MHC class I molecule HLA-C, or part thereof, and the peptide according to the invention. The exosome may be isolated from a cell arranged to express MHC class I molecule HLA-Cw*0102 and the peptide according to the invention. The exosome may be isolated from a cell arranged to express MHC class I molecule HLA-C*0304 and the peptide according to the invention.

According to another aspect of the invention, there is provided an activated NK cell, wherein the NK cell expresses KIR2DS2 receptor, and wherein the NK cell is activated by exposure to the peptide according to the invention.

The NK cell may be mammalian. The NK cell may be human. The exposure of the NK cell to the peptide to activate the NK cell may be in vitro, for example in a cell culture. The exposure of the NK cell to the peptide to activate the NK cell may cause expansion of the NK cell into multiple NK cells having specificity to specific peptides, such as the peptide according to the invention, or related peptides. One or more cytokines may additionally be added to the NK cells to aid activation and/or expansion.

According to another aspect of the invention, there is provided a nucleic acid comprising a sequence encoding a peptide according to the invention.

The nucleic acid may be a plasmid vector for vaccination. The nucleic acid may comprise DNA or RNA. The nucleic acid may comprise viral nucleic acid. The nucleic acid may comprise a viral vector. The nucleic acid may be a vector. The nucleic acid may comprise Adeno associated virus plasmid DNA. The nucleic acid may further comprise a sequence encoding an MHC class I molecule. The MHC class I molecule may comprise HLA-C, or part thereof. The MHC class I molecule may comprise HLA-Cw*0102. The MHC class I molecule may comprise HLA-C*0304. The nucleic acid may comprise a viral promoter, such as SV40 promoter, Rous Sarcoma Virus (RSV) promoter, or cytomegalovirus (CMV) immediate early promoter. The nucleic acid may comprise a sequence encoding Mason-Pfizer monkey virus (MPV)-CTE with or without rev. The nucleic acid may comprise an enhancer sequence. The nucleic acid may comprise a synthetic intron. The nucleic acid may comprise an adenovirus tripartite leader (TPL) sequence. The nucleic acid may comprise a N-terminal ubiquitin signal for targeting the MHC class I pathway. The nucleic acid may encode Adenovirus E3/19K glycoprotein. The nucleic acid may encode a 2A sequence for control of splicing, for example T2A (Thosea asigna virus 2A:T2A), F2A (foot and mouth disease virus 2A) equine rhinitis A virus (E2A), or porcine teschovirus-1 (P2A). The nucleic acid may encode E19/3K, the peptide of the invention, T2A, and a HLA-C, or part thereof. The nucleic acid may encode E19/3K:Peptide:T2A:HLA-C in the orientation provided.

According to another aspect of the invention, there is provided a virus comprising the nucleic acid according to the invention. The virus may be selected from any of the group comprising adenovirus; Adeno associated virus; Pox viruses eg vaccinia such as MVA; Alpha viruses eg Semliki forest virus; Lentivirus; Retrovirus; Oncolytic virus e.g. reovirus. The virus may be attenuated.

According to another aspect of the invention, there is provided a dendritic cell expressing, or capable of expressing, the complex according to the invention. The dendritic cell may comprise nucleic acid encoding the complex according to the invention. The dendritic cell may be autologous for the patient. For example, dendritic cell may be harvested from a patient and transformed with nucleic acid encoding the complex according to the invention. Transformants, or generations thereof, may then be returned back to the patient for treatment or prophylaxis (e.g. immunisation).

According to another aspect of the invention, there is provided an immunogenic composition comprising one or more of:
the peptide according to the invention;
the complex according to the invention;
the vesicle according to the invention;
the dendritic cell according to the invention;
the nucleic acid according to the invention; and
the virus according to the invention.

According to another aspect of the invention, there is provided an immunogenic composition comprising the peptide according to the invention.

According to another aspect of the invention, there is provided an immunogenic composition comprising the complex according to the invention.

According to another aspect of the invention, there is provided an immunogenic composition comprising the vesicle according to the invention.

According to another aspect of the invention, there is provided an immunogenic composition comprising the dendritic cell according to the invention.

According to another aspect of the invention, there is provided an immunogenic composition comprising the nucleic acid according to the invention.

According to another aspect of the invention, there is provided an immunogenic composition comprising the virus according to the invention.

The immunogenic composition may comprise a carrier, such as a pharmaceutical acceptable carrier. The carrier may comprise a buffer.

According to another aspect of the invention, there is provided a method of treatment or prophylaxis of an NK cell regulated disease comprising the administration of:
- the peptide according to the invention;
- the immunogenic composition according to the invention;
- the complex according to the invention;
- the vesicle according to the invention;
- the dendritic cell according to the invention;
- the activated NK cell according to the invention;
- the nucleic acid according to the invention; or
- the virus according to the invention.

According to another aspect of the invention, there is provided a method of treatment or prophylaxis of an NK cell regulated disease comprising the administration of the peptide according to the invention.

According to another aspect of the invention, there is provided a method of treatment or prophylaxis of an NK cell regulated disease comprising the administration of the immunogenic composition according to the invention.

According to another aspect of the invention, there is provided a method of treatment or prophylaxis of an NK cell regulated disease comprising the administration of the complex according to the invention.

According to another aspect of the invention, there is provided a method of treatment or prophylaxis of an NK cell regulated disease comprising the administration of the vesicle according to the invention.

According to another aspect of the invention, there is provided a method of treatment or prophylaxis of an NK cell regulated disease comprising the administration of the dendritic cell according to the invention.

According to another aspect of the invention, there is provided a method of treatment or prophylaxis of an NK cell regulated disease comprising the administration of the activated NK cell according to the invention.

According to another aspect of the invention, there is provided a method of treatment or prophylaxis of an NK cell regulated disease comprising the administration of the nucleic acid according to the invention.

According to another aspect of the invention, there is provided a method of treatment or prophylaxis of an NK cell regulated disease comprising the administration of the virus according to the invention.

The activated NK cells may be provided in the amount of at least $1\times10^7$ cells per kg of body weight. The activated NK cells may be provided in the amount of between about $1\times10^7$ and $5\times10^9$ cells per kg of body weight. The activated NK cells may be provided in the amount of between about $1\times10^7$ and $1\times10^9$ cells per kg of body weight.

The treatment or prophylaxis may additionally comprise the administration of one or more cytokines. The cytokine(s) may be administered in the same composition as the peptide of the invention. The administration may be intravenously. In an embodiment where cancer is to be treated, the administration may be directly into the artery supplying the cancer.

According to another aspect of the invention, there is provided an agent for use in the prophylaxis or treatment of an NK cell regulated disease, the agent comprising or consisting of:
- the peptide according to the invention;
- the immunogenic composition according to the invention;
- the complex according to the invention;
- the vesicle according to the invention;
- the dendritic cell according to the invention;
- the activated NK cell according to the invention;
- the nucleic acid according to the invention; or
- the virus according to the invention.

According to another aspect of the invention, there is provided an agent for use in the prophylaxis or treatment of an NK cell regulated disease, the agent comprising or consisting of the peptide according to the invention.

According to another aspect of the invention, there is provided an agent for use in the prophylaxis or treatment of an NK cell regulated disease, the agent comprising or consisting of the immunogenic composition according to the invention.

According to another aspect of the invention, there is provided an agent for use in the prophylaxis or treatment of an NK cell regulated disease, the agent comprising or consisting of the complex according to the invention.

According to another aspect of the invention, there is provided an agent for use in the prophylaxis or treatment of an NK cell regulated disease, the agent comprising or consisting of the vesicle according to the invention.

According to another aspect of the invention, there is provided an agent for use in the prophylaxis or treatment of an NK cell regulated disease, the agent comprising or consisting of the dendritic cell according to the invention.

According to another aspect of the invention, there is provided an agent for use in the prophylaxis or treatment of an NK cell regulated disease, the agent comprising or consisting of the activated NK cell according to the invention;

According to another aspect of the invention, there is provided an agent for use in the prophylaxis or treatment of an NK cell regulated disease, the agent comprising or consisting of the nucleic acid according to the invention.

According to another aspect of the invention, there is provided an agent for use in the prophylaxis or treatment of an NK cell regulated disease, the agent comprising or consisting of the virus according to the invention.

According to another aspect of the invention, there is provided a method of treatment or prophylaxis of a patient for an NK cell regulated disease comprising determining if a patient produces KIR2DS2-expressing NK cells;
wherein if the patient produces KIR2DS2-expressing NK cells, administering:
- the peptide according to the invention;
- the immunogenic composition according to the invention;
- the complex according to the invention;
- the vesicle according to the invention;
- the dendritic cell according to the invention;
- the nucleic acid according to the invention; or
- the virus according to the invention; and
optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
wherein if the patient produces KIR2DS2-expressing NK cells, administering the peptide according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
    wherein if the patient produces KIR2DS2-expressing NK cells, administering the immunogenic composition according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
    wherein if the patient produces KIR2DS2-expressing NK cells, administering the complex according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
    wherein if the patient produces KIR2DS2-expressing NK cells, administering the vesicle according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
    wherein if the patient produces KIR2DS2-expressing NK cells, administering the dendritic cell according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
    wherein if the patient produces KIR2DS2-expressing NK cells, administering the nucleic acid according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces KIR2DS2-expressing NK cells;
    wherein if the patient produces KIR2DS2-expressing NK cells, administering the virus according to the invention; and optionally wherein if the patient does not produce KIR2DS2-expressing NK cells, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering:
        the peptide according to the invention;
        the immunogenic composition according to the invention;
        the complex according to the invention;
        the vesicle according to the invention;
        the dendritic cell according to the invention;
        the nucleic acid according to the invention; or
        the virus according to the invention; and
    optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering the peptide according to the invention; and
    optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering the immunogenic composition according to the invention; and
    optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering the complex according to the invention; and
    optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering the vesicle according to the invention; and
    optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering the dendritic cell according to the invention; and
    optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
    wherein if the patient produces a ligand for KIR2DS2, administering the nucleic acid according to the invention; and optionally wherein if the patient does not produce a ligand for KIR2DS2, administering to the patient the activated NK cells according to the invention.

According to another aspect of the invention, there is provided a method of treatment or prophylaxis of a patient for an NK cell regulated disease comprising determining if a patient produces a ligand for KIR2DS2;
wherein if the patient produces a ligand for KIR2DS2, administering the virus according to the invention; and
optionally wherein if the patient does not produce a ligand for KIR2DS2, administering to the patient the activated NK cells according to the invention.

According to another aspect of the invention, there is provided a method of selecting a patient for treatment or prophylaxis with an agent arranged to activate NK cell mediated protection from a disease, wherein the agent is selected from:
the peptide according to the invention;
the immunogenic composition according to the invention;
the complex according to the invention;
the vesicle according to the invention;
the nucleic acid according to the invention; or
the virus according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the peptide according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the immunogenic composition according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the complex according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the vesicle according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the nucleic acid according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the virus according to the invention;
the method comprising the step of determining if the patient produces KIR2DS2-expressing NK cells,
wherein a patient producing KIR2DS2-expressing NK cells is selected for the treatment or prophylaxis with the agent; and optionally wherein a patient not producing KIR2DS2-expressing NK cells is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is selected from:
the peptide according to the invention;
the immunogenic composition according to the invention;
the complex according to the invention;
the vesicle according to the invention;
the nucleic acid according to the invention; or
the virus according to the invention;
the method comprising the step of determining if the patient produces a ligand for KIR2DS2,
wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the peptide according to the invention;

the method comprising the step of determining if the patient produces a ligand for KIR2DS2, wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the immunogenic composition according to the invention;

the method comprising the step of determining if the patient produces a ligand for KIR2DS2, wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the complex according to the invention;

the method comprising the step of determining if the patient produces a ligand for KIR2DS2, wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the vesicle according to the invention;

the method comprising the step of determining if the patient produces a ligand for KIR2DS2, wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the nucleic acid according to the invention;

the method comprising the step of determining if the patient produces a ligand for KIR2DS2, wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

According to another aspect of the invention, there is provided a method of selecting a patient for treatment or prophylaxis with an agent arranged to activate NK cell mediated protection from a disease, wherein the agent is the virus according to the invention;

the method comprising the step of determining if the patient produces a ligand for KIR2DS2, wherein a patient producing a ligand for KIR2DS2 is selected for the treatment or prophylaxis with the agent; and optionally wherein a patient not producing a ligand for KIR2DS2 is not selected for the treatment or prophylaxis with the agent, and/or is selected for an alternative treatment.

The ligand for KIR2DS2 may comprise a Group I HLA-C allele encoded ligand. The ligand for KIR2DS2 may comprise HLA-A11.

The method for selecting a patient may further comprise administering the agent to the selected patient.

The alternative treatment may comprise administering to the patient, the activated NK cell according to the invention.

Determining if a patient produces KIR2DS2-expressing NK cells may comprise providing a sample of patient blood or blood plasma and detecting KIR2DS2-expressing NK cells in the blood or blood plasma. Determining if a patient produces KIR2DS2-expressing NK cells may comprise providing a sample of patient blood or blood plasma and detecting nucleic acid encoding KIR2DS2. The detection may comprise PCR, for example using sequence specific primers (PCR-SSP). The detection may comprise nucleic acid sequencing, such as RNA sequencing. The detection may comprise antibody-mediated detection. The detection may comprise KIR2DS2 ligand-receptor binding mediated detection.

Determining if a patient produces a ligand for KIR2DS2 may comprise providing a sample of patient blood or blood plasma and detecting a ligand for KIR2DS2 in the blood or blood plasma. Determining if a patient produces a ligand for KIR2DS2 may comprise providing a sample of patient blood or blood plasma and detecting nucleic acid encoding a ligand for KIR2DS2. The detection may comprise PCR, for example using sequence specific primers (PCR-SSP). The detection may comprise nucleic acid sequencing, such as RNA sequencing. The detection may comprise antibody-mediated detection. The detection may comprise ligand-receptor binding mediated detection.

The NK cell regulated disease may be a disease capable of being inhibited, supressed, cured, alleviated or prevented by the action of specific NK cell mediated killing. The NK cell regulated disease may be a disease capable of being modified by the action of specific NK cell killing. The NK cell regulated disease may comprise a viral infection. The viral infection may comprise HCV infection. The viral infection may comprise HIV infection. The viral infection may comprise chronic viral infection, such as chronic HCV infection.

The NK cell regulated disease may comprise a KIR2DS2 mediated disease. The NK cell regulated disease may comprise an activating KIR mediated disease. The NK cell regulated disease may be any of the disease of infections selected from the group comprising cancer, HCV, HBV, HPV, Malaria, pregnancy related disorders, EBV, Kaposi sarcoma, Ebola, HSV, leprosy, and TB. The NK cell regulated disease may comprise HCV infection. The NK cell regulated disease may comprise EBV infection.

According to another aspect of the invention, there is provided a method of producing activated NK cells comprising exposing an NK cell expressing KIR2DS2 receptor to a peptide according to the invention.

The method of producing activated NK cells may be in vitro, for example in a cell culture.

According to another aspect of the invention, there is provided a method for activating an NK cell mediated immune response of a patient for recognition of an antigen comprising administration of:

the peptide according to the invention;
the complex according to the invention;
the vesicle according to the invention;
the nucleic acid according to the invention; or
the virus according to the invention.

According to another aspect of the invention, there is provided a method for activating an NK cell mediated immune response of a patient for recognition of an antigen comprising administration of the peptide according to the invention.

According to another aspect of the invention, there is provided a method for activating an NK cell mediated immune response of a patient for recognition of an antigen comprising administration of the complex according to the invention.

According to another aspect of the invention, there is provided a method for activating an NK cell mediated immune response of a patient for recognition of an antigen comprising administration of the vesicle according to the invention.

According to another aspect of the invention, there is provided a method for activating an NK cell mediated immune response of a patient for recognition of an antigen comprising administration of the nucleic acid according to the invention.

According to another aspect of the invention, there is provided a method for activating an NK cell mediated immune response of a patient for recognition of an antigen comprising administration of the virus according to the invention.

The antigen may comprise a peptide derived from HCV. The antigen may comprise a peptide derived from HIV. The antigen may comprise a peptide derived from a cancer cell. The antigen may comprise a peptide derived from, or specific for, any of the diseases of infections selected from the group comprising cancer, HCV, HBV, HPV, Malaria, pregnancy related disorders, EBV, Kaposi sarcoma, Ebola, HSV, leprosy, and TB. The NK cell regulated disease may comprise HCV infection.

The immune response may be protective.

According to another aspect of the invention, there is provided a peptide according to the invention for use in, or as, a vaccine.

The term "immunogenic", when applied to the peptide or composition of the present invention means capable of eliciting an immune response in a human or animal body.

The term "isolated", when applied to the peptide or complex of the present invention means a peptide or complex: (i) encoded by nucleic acids using recombinant DNA methods; or (ii); synthesized by, for example, chemical synthetic methods; or (iii) separated from naturally-occurring biological materials, and then purified using protein analytical procedures; or (iv) associated with chemical moieties (e.g. peptides, carbohydrates, fatty acids, and the like) other than those associated with the antigenic peptide in its naturally-occurring state; or (v) that do not occur in nature. An isolated peptide or complex of the invention includes a peptide or complex expressed from a nucleotide sequence encoding the peptide or complex, or from a recombinant vector containing a nucleotide sequence encoding the peptide or complex.

The term "protective" means prevention of a disease, a reduced risk of disease infection, transmission and/or progression, reduced severity of disease, a cure of a condition or disease, an alleviation of symptoms, or a reduction in severity of a disease or disease symptoms.

The term "prophylaxis" means prevention of or protective treatment for a disease. The prophylaxis may include a reduced risk of disease infection, transmission and/or progression, or reduced severity of disease.

The term "treatment", means a cure of a condition or disease, an alleviation of symptoms, or a reduction in severity of a disease or disease symptoms.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1 shows that the peptide LNPSVAATL (SEQ ID NO: 1) binds HLA-Cw*0102. The HLA-Cw*0102-positive cell line L721.174 was incubated with increasing concentrations of the LNPSVAATL (SEQ ID NO: 1) peptide or a control peptide VAPWNSLSL (SEQ ID NO: 48). Cells were stained for cell surface of MHC class I and analysed by flow cytometry. The mean fluorescence intensity of cell surface MHC Class I was plotted against the peptide concentration.

Figure 2:
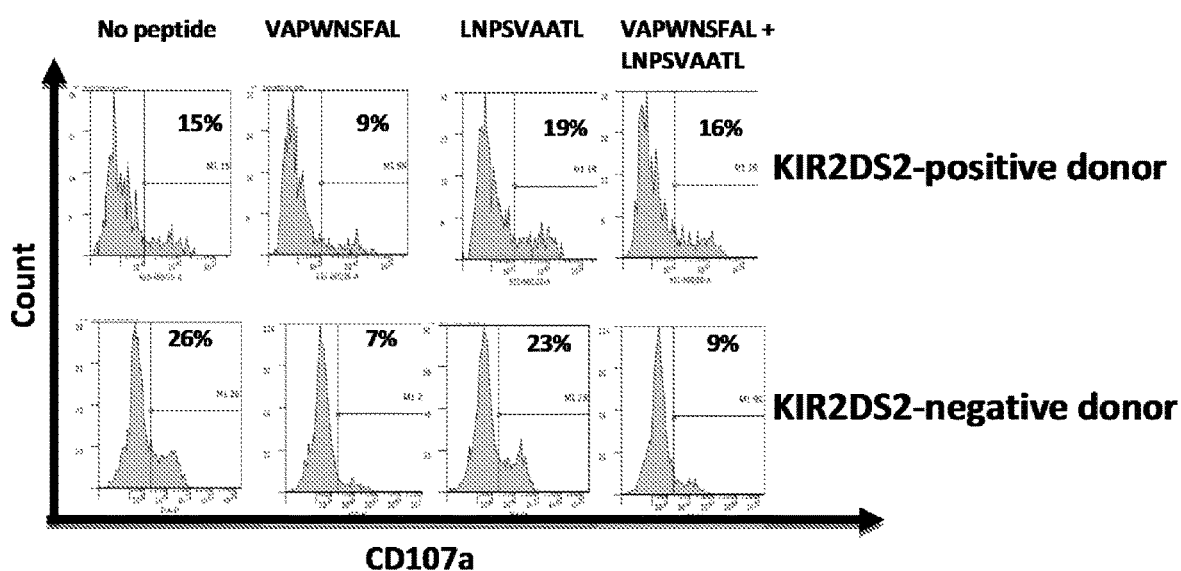
Figure 2:
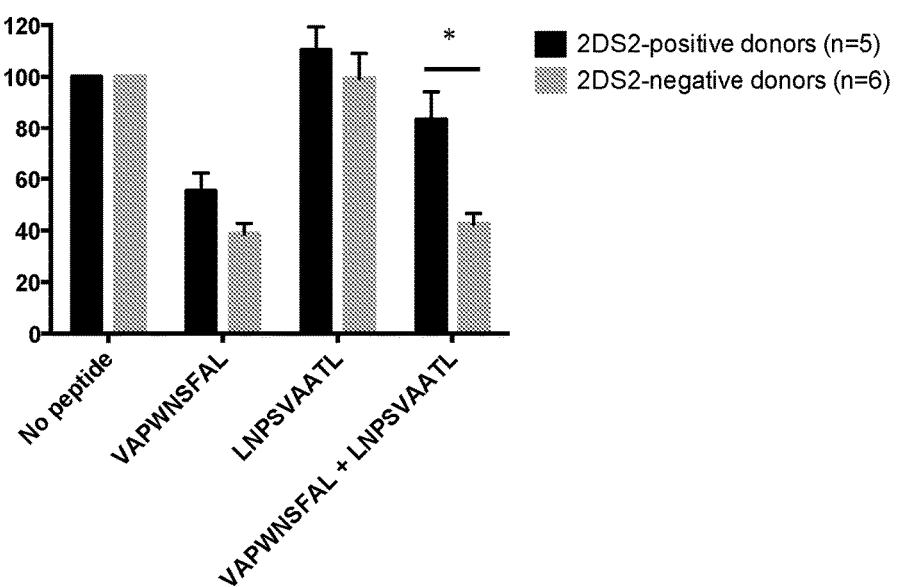

FIG. 2 shows that LNPSVAATL (SEQ ID NO: 1) is recognized by KIR2DS2-positive NK cells and leads to NK cell activation (CD107a degranulation), and killing of target cells expressing HLA-Cw*0102. A. cells were incubated in the presence or absence of peptides, and then cultured with NK cells from either a KIR2DS2-positive or KIR2DS2-negative donor. The level of CD107a (LAMP) expression was measured on NK cells positive for the CH-L antibody. This antibody binds to KIR2DS2, KIR2DL2 and KIR2DL3. B. Summary data from 5 KIR2DS2-positive and 6 KIR2DS2-negative donors tested as per panel A of FIG. 2. To compare the different donors the data are normalized to 100% for the no peptide condition.

Figure 3:
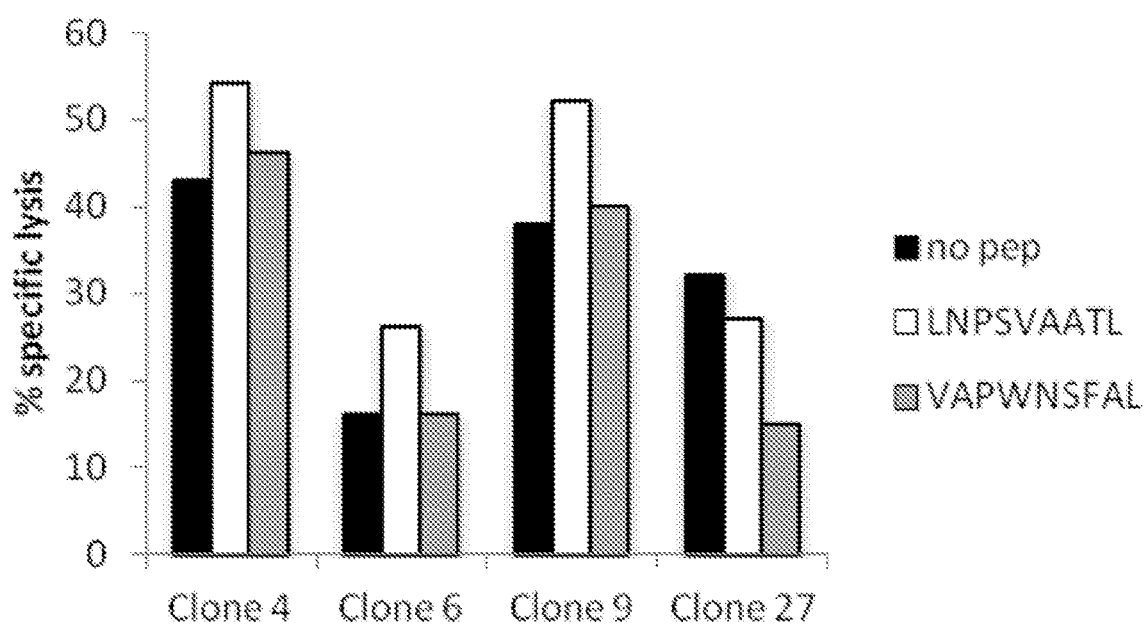

FIG. 3 shows that KIR2DS2-postive NK cell clones kill target cells expressing HLA-Cw*0102 and the LNPSVAATL (SEQ ID NO: 1) peptide. L721.174 cells were incubated in the presence or absence of the peptides VAPWNSFAL (SEQ ID NO: 49) and the LNPSVAATL (SEQ ID NO: 1). The cells were then labeled with the cell tracker orange dye, and then cultured with KIR2DS2-positive NK cell clones (clones 4,6,9) or a KIR2DS2-negative NK cell clone (clone 27). Cytotoxicity was then determined using Live/Dead® fixable far-red stain.

Figure 4:
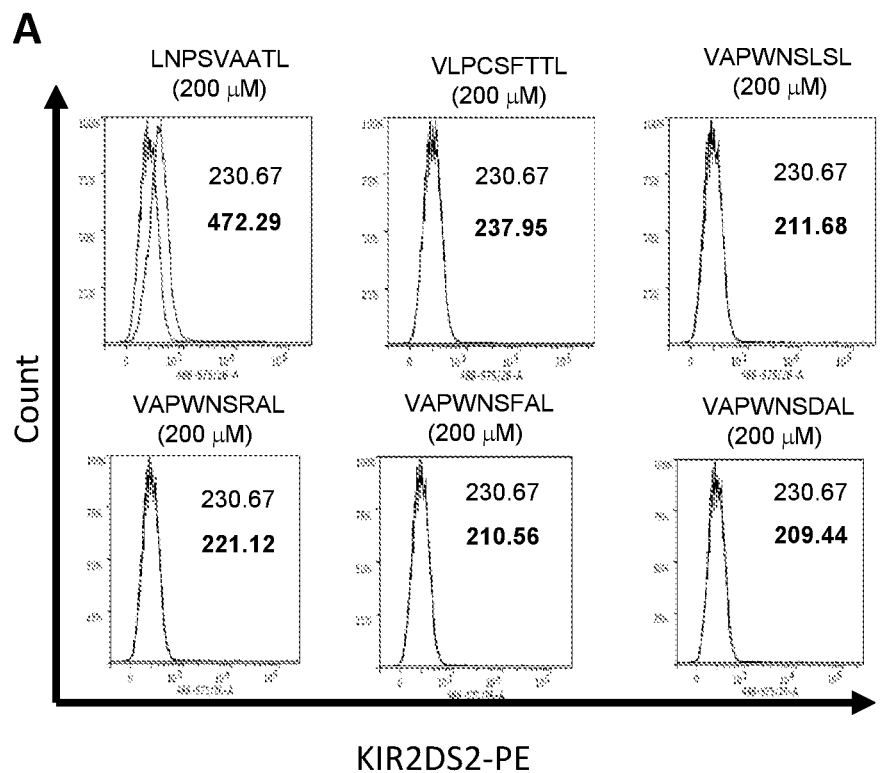
Figure 4:
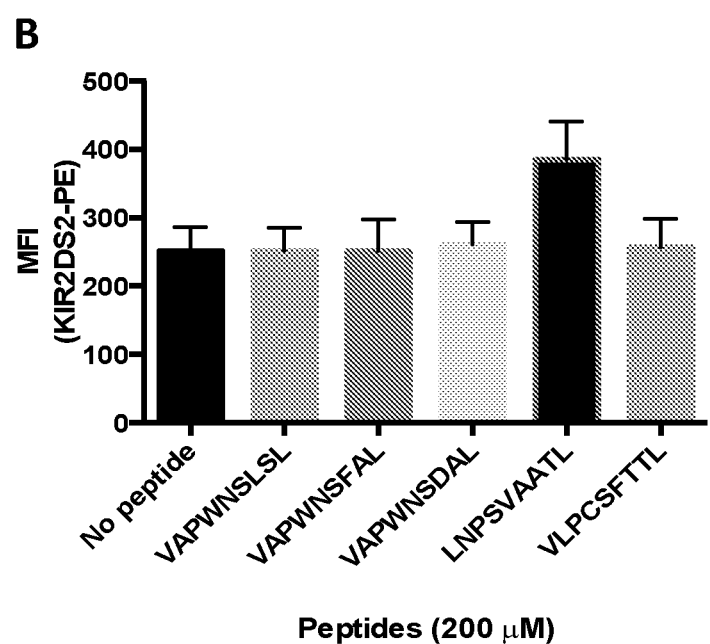

FIG. 4 shows that KIR2DS2 binds to HLA-C*0102 and the LNPSVAATL (SEQ ID NO: 1) peptide. A. The KIR2DS2 protein was expressed with a biotinylation C-terminal tag. Following biotinylation with the BirA enzyme, the KIR2DS2 protein was incubated with streptavidin-phycoerythrin to form fluorescent KIR2DS2-tetramers (KIR2DS2-PE). L721.174 cells were then incubated with indicated peptides. Cells were then stained with KIR2DS2-PE and analysed by flow cytometry. Shown are histogram plots. The bold numbers represent the mean fluorescent staining intensity of the KIR2DS2-PE staining of the cells in the presence of peptide and the non-bold numbers the staining in the absence of peptide. B. Represents the mean and standard error fluorescent intensities of the experiment in "A" following replicate experiments.

Figure 5:
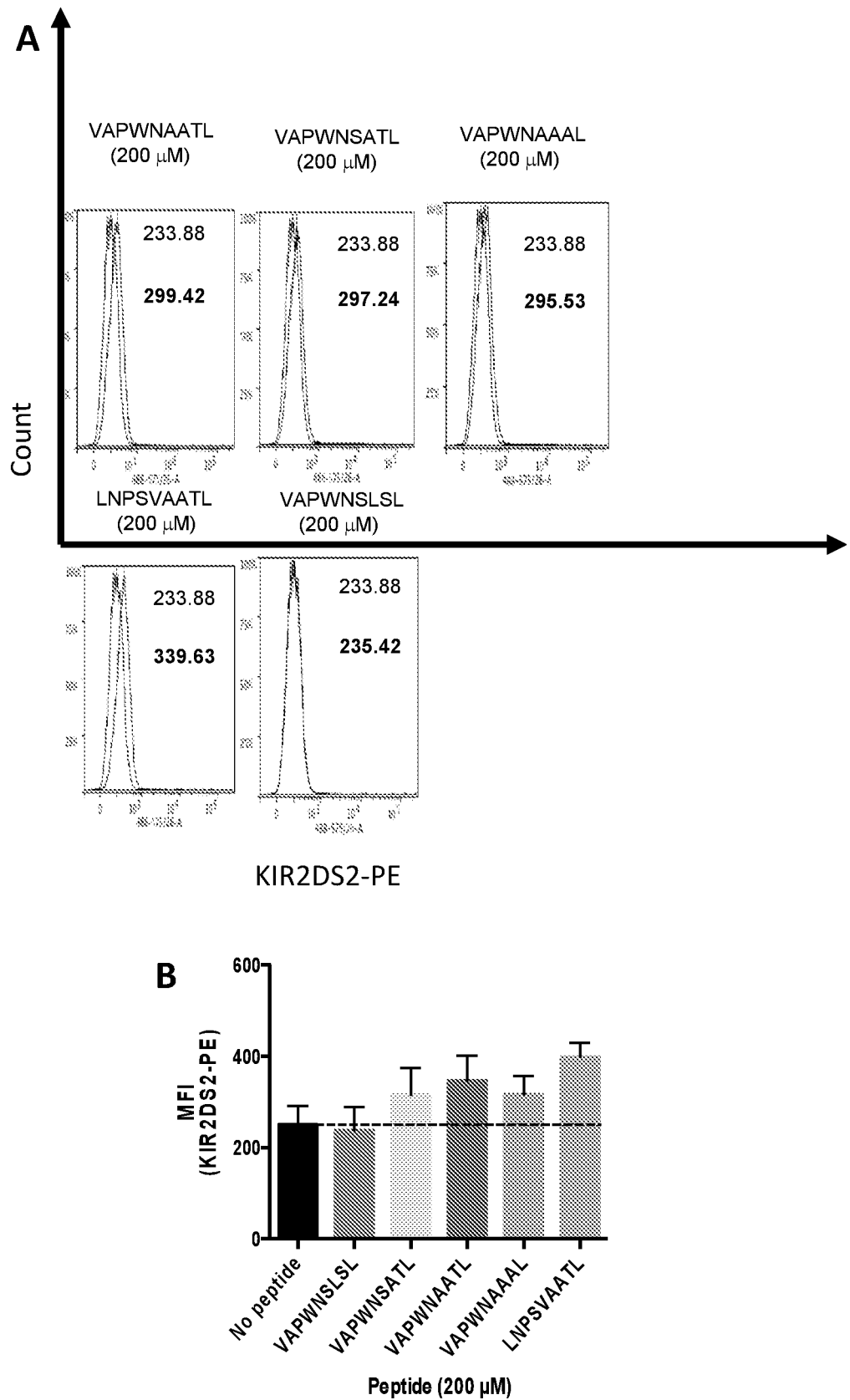

FIG. 5 shows that KIR2DS2 recognises peptides with XXXXXAAL (SEQ ID NO: 50) and XXXXXATL (SEQ ID NO: 51) motifs. A. L721.174 cells were incubated with indicated peptides. Cells were then stained with KIR2DS2-PE (see FIG. 4) and analysed by flow cytometry. Shown are histogram plots. The bold numbers represent the mean fluorescent staining intensity of the KIR2DS2-PE staining of the cells in the presence of peptide and the non-bold numbers the staining in the absence of peptide. B. Represents the mean and standard error fluorescent intensities of the experiment in "A" following replicate experiments.

Figure 6:
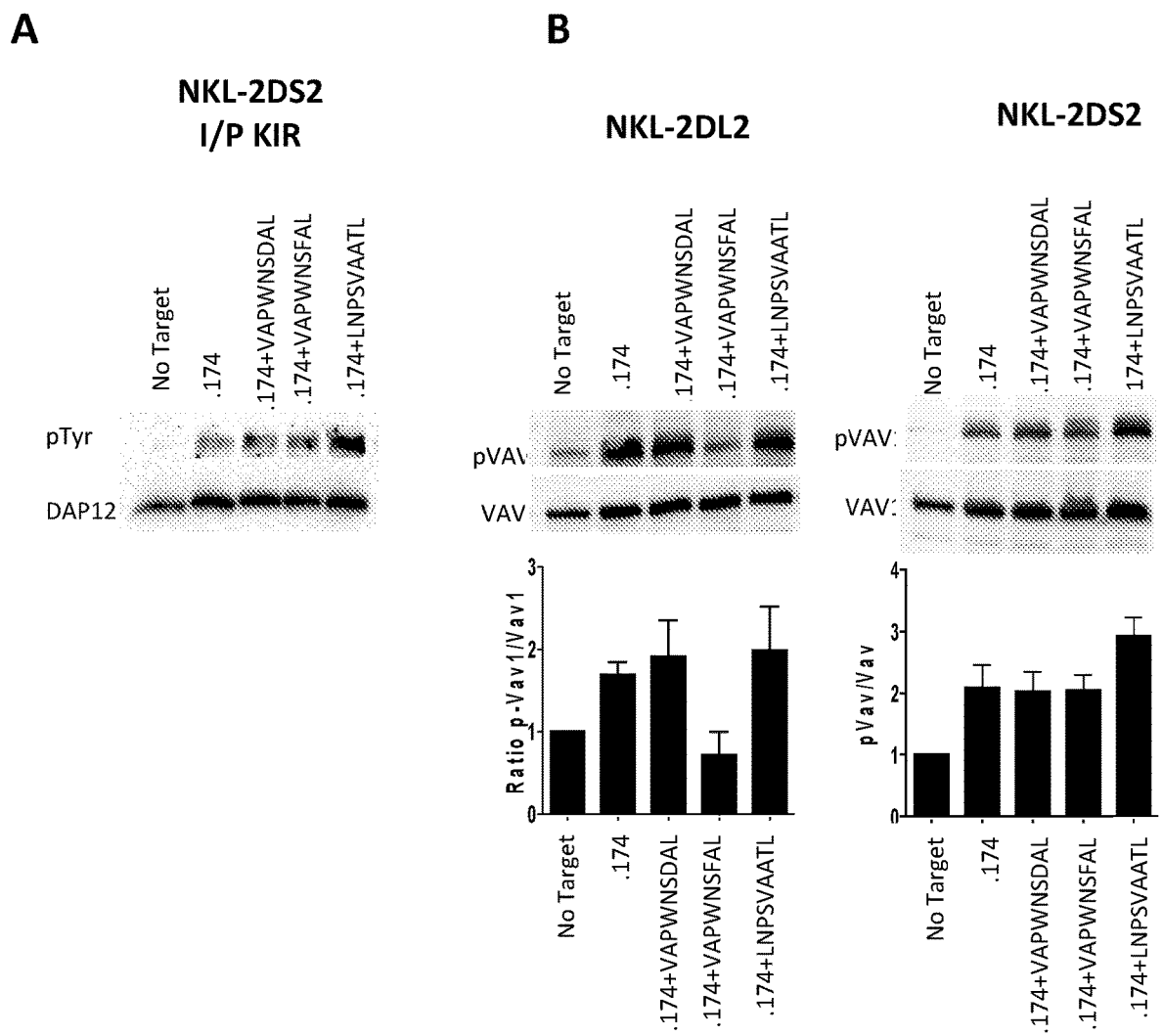

FIG. 6 LNPSVAATL (SEQ ID NO: 1) activates NK cells expressing KIR2DS2. A. L721.174 cells were incubated with indicated peptides. The cells were then incubated with the NK cell line transfected with KIR2DS2. The cells were lysed and the KIR2DS2 was then immunoprecipitated from the mixture using the GL183 antibody coupled to protein-G beads. The immune precipitate was analysed by Western blotting using a phosphotyrosine antibody. The membrane was then stripped and reprobed with an antibody to DAP12 the molecule that transduces a positive signal from KIR2DS2. Shown are the regions on the blots at the level of DAP12 (12-15kDa). B. L721.174 cells were incubated with indicated peptides. The cells were then incubated with the NK cell line transfected with KIR2DS2 or transfected with KIR2DL2. The cells were lysed in 1% NP-40 and then analysed by Western blotting using antibodies to pVav1 and then following stripping of the membrane to Vav1. Shown are Western blots around the 98 kDa region, and below them the corresponding densitometries for 3 independent experiments.

Figure 7:
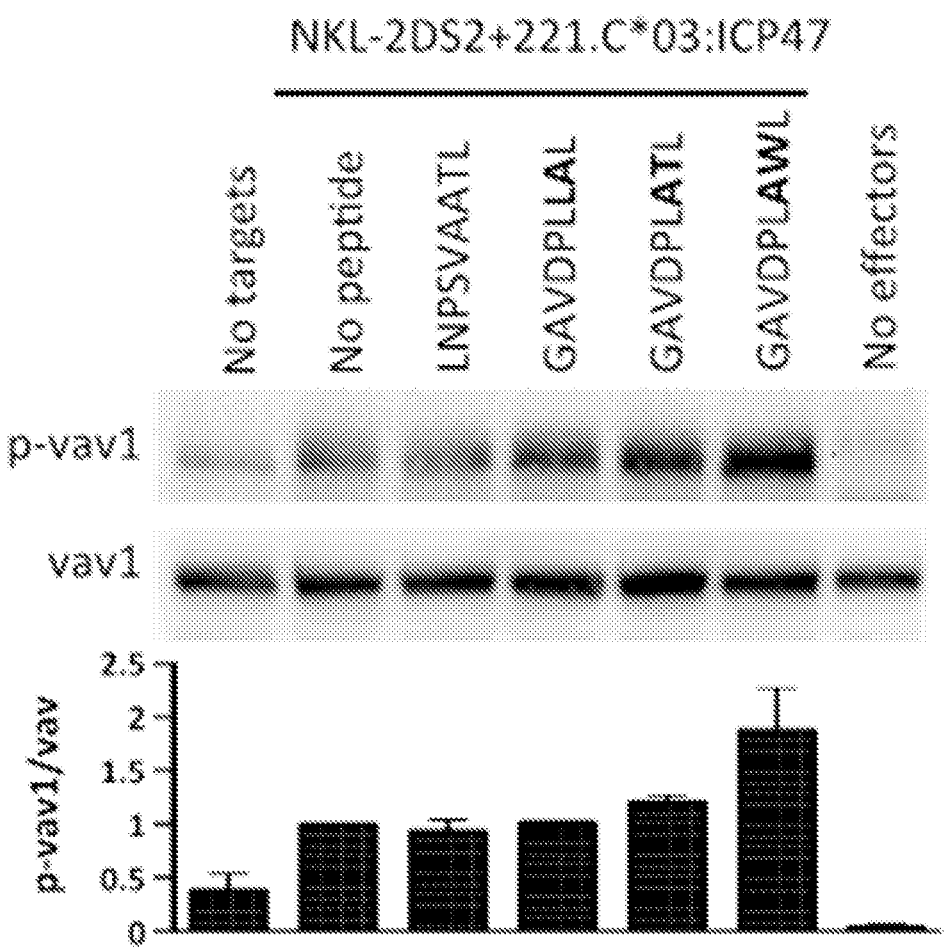

FIG. 7 $1 \times 10^6$ L721.221-HLA-C*0304-ICP47 cells were incubated overnight at 26° C. with indicated peptides at a concentration of 20 μM. The cells were then incubated with the NKL cell line transfected with KIR2DS2 or transfected with KIR2DL2 for 5 minutes. The cells were lysed in 1% NP-40 and then analysed by Western blotting using antibodies to pVav1 and then following stripping of the membrane to Vav1. Shown are Western blots around the 98 kDa region, and below them the corresponding densitometries for 2 independent experiments.

Figure 8:
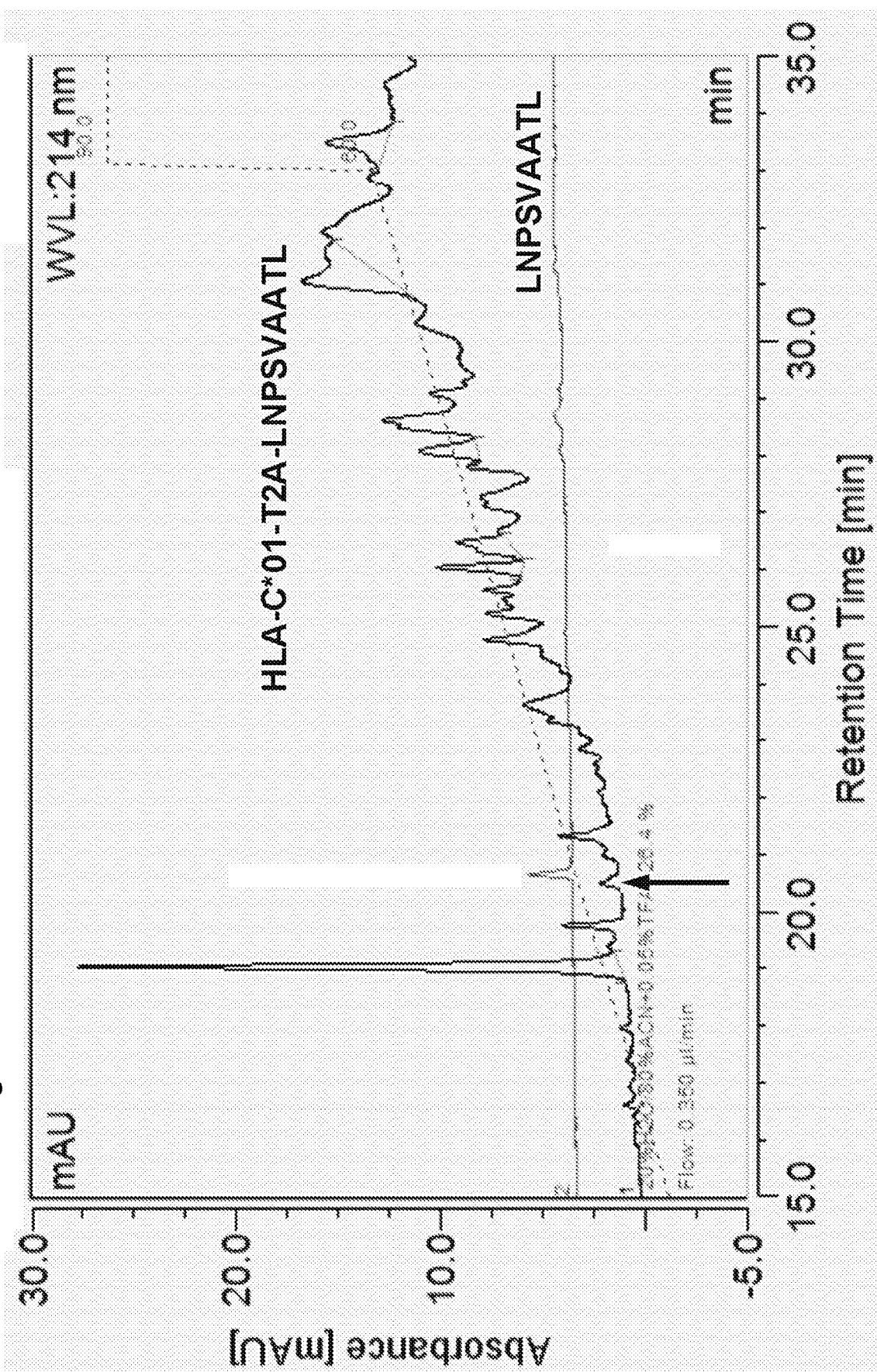

FIG. 8 The MHC class I-negative 721.221 cell line was transfected with a construct expressing HLA-C*0102:T2A:E19/3K:LNPSVAATL (SEQ ID NO: 1). The cells were washed and then the HLA-C binding peptides eluted using 10% acetic acid. The eluate was analysed by HPLC using a C18 column and a 4-60% acetonitrile gradient. The resulting profile was compared to the profile of the LNPSVAATL (SEQ ID NO: 1) peptide alone. The peptide elution peak is indicated with an arrow.

Figure 9:
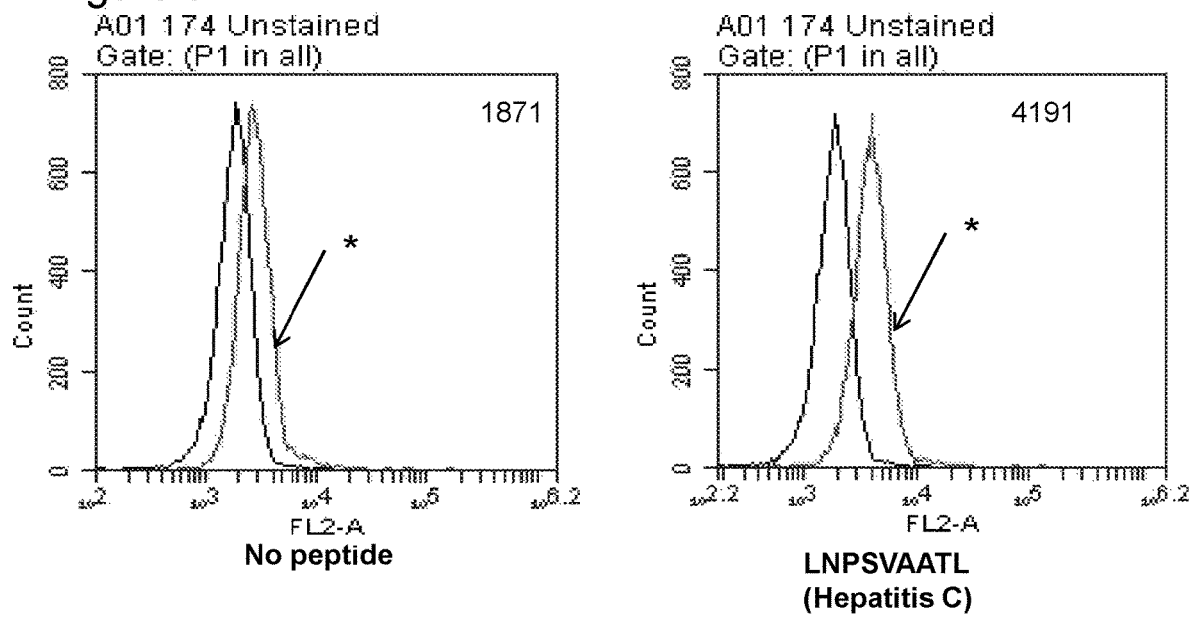

FIG. 9—shows KIR2DS2 tetramer staining on 174 cells with and without the peptides. Staining comparison with the unstained cells, MFI of stained cells (indicated by *) is shown.

EXAMPLE 1

KIR2DS1 and its Group 1 HLA-C Ligands Provide Protection Against Chronic Hepatitis C Virus (HCV) Infection Table 1 shows a logistic regression analysis of the outcome of HCV infection and its association with KIR and HLA in 272 individuals exposed to HCV. 180 individuals had chronic infection and 92 cleared infection. An odds ratio (OR)>1 indicates protection against chronic HCV infection. (HLA-C*0102 is one of the group 1 HLA-C alleles).

TABLE 1

KIR2DS1 and its group 1 HLA-C ligands provide protection against chronic hepatitis C virus (HCV) infection.

|  | P | OR | 95% CI |
| --- | --- | --- | --- |
| KIR2DL3: HLA-C1C1 | 0.006 | 2.56 | 1.31-5.02 |
| KIR2DS3 | 0.027 | 0.50 | 0.28-0.92 |
| KIR2DS2: group 1 HLA-C | 0.033 | 1.83 | 1.05-3.19 |
| KIR3DS1: HLA-Bw4 | 0.076 | 1.83 | 0.94-3.55 |
| KIR2DS1: HLA-C2 | 0.176 | 0.60 | 0.29-1.25 |

EXAMPLE 2

The Peptide LNPSVAATL (SEQ ID NO: 1) Binds HLA-Cw*0102

With reference to FIG. 1, the HLA-Cw*0102-positive cell line L721.174 was incubated with increasing concentrations of the LNPSVAATL (SEQ ID NO: 1) peptide or a control peptide VAPWNSLSL (SEQ ID NO: 48) (known to bind HLA-Cw*0102) overnight at 26° C. $3 \times 10^5$ cells were used per condition. Following washing in PBS the cells were stained for cell surface of MHC class I and analysed by flow cytometry. The mean fluorescence intensity of cell surface MHC Class I was plotted against the peptide concentration.

EXAMPLE 3

LNPSVAATL (SEQ ID NO: 1) is Recognized by KIR2DS2-Positive NK Cells and Leads to NK Cell Activation (CD107a Degranulation), and Killing of Target Cells Expressing HLA-Cw*0102

With reference to FIG. 2A, $3 \times 10^5$ L721.174 cells were incubated at 26° C. overnight in the presence or absence of peptides, and then cultured for four hours with NK cells from either a KIR2DS2-positive or KIR2DS2-negative donor. The level of CD107a (LAMP) expression was measured on NK cells positive for the CH-L antibody. This antibody binds to KIR2DS2, KIR2DL2 and KIR2DL3. NK cells from both donors have lower levels of degranulation when exposed to the VAP-FA (VAPWNSFAL) (SEQ ID NO: 49) peptide as compared to no peptide. NK cells from the KIR2DS2-positive donors have higher levels of degranulation when exposed to the LNPSVAATL peptide as compared to no peptide. NK cells from the KIR2DS2-positive donors have higher levels of degranulation when exposed to the VAPWNSFAL (SEQ ID NO: 49) and the LNPSVAATL (SEQ ID NO: 1) peptide in combination as compared to the VAPWNSFAL (SEQ ID NO: 49) peptide alone. With reference to FIG. 2B, summary data from 5 KIR2DS2-positive and 6 KIR2DS2-negative donors were tested as per panel A of FIG. 2. To compare the different donors the data are normalized to 100% for the no peptide condition.

EXAMPLE 4

KIR2DS2-Postive NK Cell Clones Kill Target Cells Expressing HLA-Cw*0102 and the LNPSVAATL (SEQ ID NO: 1) Peptide With reference to FIG. 3, $3 \times 10^5$ L721.174 cells were incubated at 26° C. overnight in the presence or absence of the peptides VAPWNSFAL (SEQ ID NO: 49) and the LNPSVAATL (SEQ ID NO: 1). The cells were then labeled with the cell tracker orange dye, and then cultured for four hours with KIR2DS2-positive NK cell clones (clones 4,6,9) or a KIR2DS2-negative NK cell clone (clone 27). Cytotoxicity was then determined using Live/Dead® fixable far-red stain. Only clones 4, 6, 9 killed the L721.174 cell line to greater extent in the presence of the LNPSVAATL (SEQ ID NO: 1) peptide as compared to no peptide or the VAPWNSFAL (SEQ ID NO: 49) peptide.

EXAMPLE 5

KIR2DS2 Binds to HLA-C*0102 and the LNPSVAATL (SEQ ID NO: 1) Peptide

With reference to FIG. 4A, the KIR2DS2 protein was expressed as a recombinant protein with a biotinylation C-terminal tag. Following biotinylation with the BirA enzyme, the KIR2DS2 protein was incubated with streptavidin-phycoerythrin to form fluorescent KIR2DS2-tetramers (KIR2DS2-PE). $3\times10^5$ L721.174 cells were then incubated overnight at 26° C. with indicated peptides at a concentration of 200 µM. Cells were then stained with KIR2DS2-PE and analysed by flow cytometry. Shown are histogram plots. The bold numbers represent the mean fluorescent staining intensity of the KIR2DS2-PE staining of the cells in the presence of peptide and the non-bold numbers the staining in the absence of peptide. With reference to FIG. 4B, panel B represents the mean and standard error fluorescent intensities of the experiment in "A" following replicate experiments.

EXAMPLE 6

KIR2DS2 Recognises Peptides with XXXXXAAL (SEQ ID NO: 50) and XXXXXATL (SEQ ID NO: 51) Motifs With reference to FIG. 5A, $3\times10^5$ L721.174 cells were incubated overnight at 26° C. with indicated peptides at a concentration of 200 µM. Cells were then stained with KIR2DS2-PE (see FIG. 4) and analysed by flow cytometry. Shown are histogram plots. The bold numbers represent the mean fluorescent staining intensity of the KIR2DS2-PE staining of the cells in the presence of peptide and the non-bold numbers the staining in the absence of peptide. With reference to FIG. 5B, panel B represents the mean and standard error fluorescent intensities of the experiment in "A" following replicate experiments.

EXAMPLE 7

LNPSVAATL (SEQ ID NO: 1) Activates NK Cells Expressing KIR2DS2

With reference to FIG. 6A, $1\times10^6$ L721.174 cells were incubated overnight at 26° C. with indicated peptides at a concentration of 20 µM. The cells were then incubated with the NK cell line transfected with KIR2DS2 for 5 minutes. The cells were lysed in 1% digitonin buffer and the KIR2DS2 was then immunoprecipitated from the mixture using the GL183 antibody coupled to protein-G beads. The immune precipitate was analysed by Western blotting using a phosphotyrosine antibody. The membrane was then stripped and reprobed with an antibody to DAP12 the molecule that transduces a positive signal from KIR2DS2. Shown are the regions on the blots at the level of DAP12 (12-15 kDa). The LNPSVAATL (SEQ ID NO: 1) peptide induces phosphorylation of DAP12. With reference to FIG. 6B, $1\times10^6$ L721.174 cells were incubated overnight at 26° C. with indicated peptides at a concentration of 20 µM. The cells were then incubated with the NK cell line transfected with KIR2DS2 or transfected with KIR2DL2 for 5 minutes. The cells were lysed in 1% NP-40 and then analysed by Western blotting using antibodies to pVav1 and then following stripping of the membrane to Vav1. Shown are Western blots around the 98kDa region, and below them the corresponding densitometries for 3 independent experiments.

EXAMPLE 8

KIR2DS2 is Activated by the Peptide GAVPDLAWL (SEQ ID NO: 15) and GAVPDLATL (SEQ ID NO: 16)

With reference to FIG. 7, $1\times10^6$ HLA-C*0304:ICP47: 721.221 cells were incubated overnight at 26° C. with indicated peptides at a concentration of 20 µM. The cells were then incubated with the NK cell line transfected with KIR2DS2 for 5 minutes. The cells were lysed in 1% NP-40 and then analysed by Western blotting using antibodies to pVav1 and then following stripping of the membrane to Vav1. Shown is a Western blots around the 98kDa region, and below them the corresponding densitometries for 3 independent experiments.

EXAMPLE 9

FIG. 8 shows the elution profile of the peptide in a construct HLA-C:T2A:E19/3K:Peptide (FIG. 8). The cell line 721.221 expressing HLA-C*0102:T2A:E19/3K: LNPSVAATL. Following elution of the HLA-C binding peptides using 10% acetic acid the peptides were analysed by HPLC using a C18 column and an acetonitrile gradient. When compared to the control LNPSVAATL (SEQ ID NO: 1) peptide a peak is seen in the peptide eluate that corresponds to the reterntion time of the LNPSVAATL (SEQ ID NO: 1) peptide indicating that it is endogenously processed and presented and that this is a suitable vaccine construct.

REFERENCES

1. Khakoo S I, et al. HLA and NK cell inhibitory receptor genes in resolving hepatitis C virus infection. *Science*. 2004; 305(5685):872-4.
2. Martin M P, et al. Epistatic interaction between KIR3DS1 and HLA-B delays the progression to AIDS. *Nat Genet*. 2002; 31(4):429-34.
3. Deshpande A, Wheeler C M, Hunt W C, Peyton C L, White P S, Valdez Y E, Nolan J P. Variation in HLA class I antigen-processing genes and susceptibility to human papillomavirus type 16-associated cervical cancer. *J Infect Dis*. 2008; 197 (3): 371-81.
4. Carrington M, et al. Hierarchy of resistance to cervical neoplasia mediated by combinations of killer immunoglobulin-like receptor and human leukocyte antigen loci. *J Exp Med*. 2005; 201(7):1069-75.
5. Hirayasu K, et al. Significant Association of KIR2DL3-HLA-C1 Combination with Cerebral Malaria and Implications for Co-evolution of KIR and HLA. *PLoS Pathog*. 2012; 8(3):e1002565.
6. Lopez-Vazquez A, et al. Protective Effect of the HLA-Bw4I80 Epitope and the Killer Cell Immunoglobulin-Like Receptor 3DS1 Gene against the Development of Hepatocellular Carcinoma in Patients with Hepatitis C Virus Infection. *J Infect Dis.* 2005; 192(1):162-5.

7. Pan N, et al. KIR and HLA loci are associated with hepatocellular carcinoma development in patients with hepatitis B virus infection: a case-control study. *PLoS ONE.* 2011; 6(10):e25682.

8. Hiby S E, et al. Maternal activating KIRs protect against human reproductive failure mediated by fetal HLA-C2. *J Clin Invest.* 2010; 120(11):4102-10.

9. Marcus A, Raulet D H. Evidence for natural killer cell memory. *Curr Biol.* 2013; 23(17):R817-20.

10. Sun J C, Beilke J N, Lanier L L. Adaptive immune features of natural killer cells. *Nature.* 2009; 457(7229):557-61.

11. Paust S, von Andrian U H. Natural killer cell memory. *Nature Immunology.* 2011; 131(6):500-8.

12. Beziat V, et al. CMV drives clonal expansion of NKG2C+ NK cells expressing self-specific KIRs in chronic hepatitis patients. *Eur J Immunol.* 2012; 42(2):447-57.

13. Beziat V, et al. NK cell responses to cytomegalovirus infection lead to stable imprints in the human KIR repertoire and involve activating KIRs. *Blood.* 2013; 121(14):2678-88.

14. Bjorkstrom N K, et al. Rapid expansion and long-term persistence of elevated NK cell numbers in humans infected with hantavirus. *J Exp Med.* 2011; 208(1):13-21.

15. Petitdemange C, Becquart P, Wauquier N, Beziat V, Debre P, Leroy E M, Vieillard V. Unconventional repertoire profile is imprinted during acute chikungunya infection for natural killer cells polarization toward cytotoxicity. *PLoS Pathog.* 2011; 7(9):e1002268.

16. Alter G, Jost S, Rihn S, Reyor L L, Nolan B E, Ghebremichael M, Bosch R, Altfeld M, Lauer G M. Reduced frequencies of NKp30+NKp46+, CD161+ and NKG2D+ NK cells in acute HCV infection may predict viral clearance. *J Hepatol.* 2010.

17. Alter G, Rihn S, Walter K, Nolting A, Martin M, Rosenberg E S, Miller J S, Carrington M, Altfeld M. HLA class I subtype-dependent expansion of KIR3DS1+ and KIR3DL1+ NK cells during acute human immunodeficiency virus type 1 infection. *J Virol.* 2009; 83(13):6798-805.

18. Malnati M S, Peruzzi M, Parker K C, Biddison W E, Ciccone E, Moretta A, Long E O. Peptide specificity in the recognition of MHC class I by natural killer cell clones. *Science.* 1995; 267(5200):1016-8.

19. Fadda L, et al. Peptide antagonism as a mechanism for NK cell activation. *Proc Natl Acad Sci USA.* 2010; 107(22):10160-5.

20. Cheent K S, Jamil K M, Cassidy S, Liu M, Mbiribindi B, Mulder A, Claas F H, Purbhoo M A, Khakoo S I. Synergistic inhibition of natural killer cells by the nonsignaling molecule CD94. *Proc Natl Acad Sci USA.* 2013; 110(42):16981-6.

21. Croft N P, Smith S A, Wong Y C, Tan C T, Dudek N L, Flesch I E, Lin L C, Tscharke D C, Purcell A W. Kinetics of antigen expression and epitope presentation during virus infection. *PLoS Pathog.* 2013; 9(1):e1003129.

22. Moesta A K, Parham P. Diverse functionality among human NK cell receptors for the C1 epitope of HLA-C: KIR2DS2, KIR2DL2, and KIR2DL3. *Frontiers in immunology.* 2012; 3:336.

23. Korner C, Altfeld M. Role of KIR3DS1 in human diseases. *Frontiers in immunology.* 2012; 3:326.

24. David G, Djaoud Z, Willem C, Legrand N, Rettman P, Gagne K, Cesbron A, Retiere C. Large spectrum of HLA-C recognition by killer Ig-like receptor (KIR)2DL2 and KIR2DL3 and restricted C1 specificty of KIR2DS2: dominant impact of KIR2DL2/KIR2DS2 on KIR2D NK cell repertoire formation. *J Immunol.* 2013; 191(9):4778-88.

25. Knapp S, et al. Consistent beneficial effects of killer cell immunoglobulin-like receptor 2DL3 and group 1 human leukocyte antigen-C following exposure to hepatitis C virus. *Hepatology.* 2010; 51(4): 1168-75. (Khakoo Senior Author)

26. Rammensee H, Bachmann J, Emmerich N P, Bachor O A, Stevanovic S. SYFPEITHI: database for MHC ligands and peptide motifs. *Immunogenetics.* 1999; 50(3-4):213-9.

27. Gatfield J, et al. Cell lines transfected with the TAP inhibitor ICP47 allow testing peptide binding to a variety of HLA class I molecules. *Int Immunol.* 1998; 10(11):1665-72.

28. Seidel SA, et al. Microscale thermophoresis quantifies biomolecular interactions under previously challenging conditions. *Methods.* 2013; 59(3):301-15.

29. Wienken C J, Baaske P, Rothbauer U, Braun D, Duhr S. Protein-binding assays in biological liquids using microscale thermophoresis. *Nature communications.* 2010; 1:100.

30. Suppiah V, et al. IL28B, HLA-C, and KIR variants additively predict response to therapy in chronic hepatitis C virus infection in a European Cohort: a cross-sectional study. *PLoS Med.* 2011; 8(9):e1001092.

31. Borhis G, Ahmed P S, Mbiribindi B, Naiyer M M, Davis D M, Purbhoo M A, Khakoo S I. A Peptide Antagonist Disrupts NK Cell Inhibitory Synapse Formation. *J Immunol.* 2013.

32. Stewart C A, et al. Recognition of peptide-MHC class I complexes by activating killer immunoglobulin-like receptors. *Proc Natl Acad Sci USA.* 2005; 102(37): 13224-9.

33. Harrison R J, Ettorre A, Little A M, Khakoo S I. Association of NKG2A with treatment for chronic hepatitis C virus infection. *Clin Exp Immunol.* 2010; 161(2):306-14.

34. Anton L C, Yewdell J W, Bennink J R. MHC class I-associated peptides produced from endogenous gene products with vastly different efficiencies. *J Immunol.* 1997; 158(6):2535-42.

35. Liberatore C, Capanni M, Albi N, Volpi I, Urbani E, Ruggeri L, Mencarelli A, Grignani F, Velardi A. Natural killer cell-mediated lysis of autologous cells modified by gene therapy. *J Exp Med.* 1999; 189(12):1855-62.

36. Minskaia E, Ryan M D. Protein coexpression using FMDV 2A: effect of "linker" residues. *BioMed research international.* 2013; 2013:291730.

37. Tomasello E, et al. Gene structure, expression pattern, and biological activity of mouse killer cell activating receptor-associated protein (KARAP)/DAP-12. *J Biol Chem.* 1998; 273(51):34115-9.

38. Peng H, Jiang X, Chen Y, Sojka D K, Wei H, Gao X, Sun R, Yokoyama W M, Tian Z. Liver-resident NK cells confer adaptive immunity in skin-contact inflammation. *J Clin Invest.* 2013; 123(4): 1444-56.

The invention claimed is:

1. A nucleic acid comprising a sequence encoding a peptide and a sequence encoding an MHC class I HLA-C molecule, wherein the peptide consists of the amino acid sequence $X'' AX^2X^1$,
wherein:
$X''$ is an amino acid sequence of 5 or 6 residues;
$X^1$ is any amino acid; and
$X^2$ is alanine, threonine, tryptophan, or serine.

2. The nucleic acid of claim 1, wherein the nucleic acid is a plasmid vector for vaccination.

3. The nucleic acid of claim 1, wherein $X^1$ is leucine or isoleucine.

4. The nucleic acid of claim 1, wherein $X^2$ is alanine or threonine.

5. The nucleic acid of claim 1, wherein $X^2$ is tryptophan or threonine.

6. The nucleic acid of claim 1, wherein the amino acid sequence consists of LNPSVAATL (SEQ ID NO: 1); NPSVAATL (SEQ ID NO: 2); PSVAATL (SEQ ID NO: 3); VAPWNAATL (SEQ ID NO: 4); APWNAATL (SEQ ID NO: 5); PWNAATL (SEQ ID NO: 6); VAPWNSATL (SEQ ID NO: 7); APWNSATL (SEQ ID NO: 8); PWNSATL (SEQ ID NO: 9); VAPWNSAAL (SEQ ID NO: 10); APWNSAAL (SEQ ID NO: 11); PWNSAAL (SEQ ID NO: 12); VAPWNAAAL (SEQ ID NO: 13); APWNAAAL (SEQ ID NO: 14); PWNAAAL (SEQ ID NO: 17); LNPSVAATI (SEQ ID NO: 18); NPSVAATI (SEQ ID NO: 19); PSVAATI (SEQ ID NO: 20); VAPWNAATI (SEQ ID NO: 21); APWNAATI (SEQ ID NO: 22); PWNAATI (SEQ ID NO: 23); VAPWNSATI (SEQ ID NO: 24); APWNSATI (SEQ ID NO: 25); PWNSATI (SEQ ID NO: 26); VAPWNSAAI (SEQ ID NO: 27); APWNSAAI (SEQ ID NO: 28); PWNSAAI (SEQ ID NO: 29); LNPSVAAAL (SEQ ID NO: 30); NPSVAAAL (SEQ ID NO: 31); PSVAAAL (SEQ ID NO: 32); LNPSVAASL (SEQ ID NO: 33); NPSVAASL (SEQ ID NO: 34); PSVAASL (SEQ ID NO: 35); LNPSVAAWL (SEQ ID NO: 36); NPSVAAWL (SEQ ID NO: 37); PSVAAWL (SEQ ID NO: 38); LNPSVAAAI (SEQ ID NO: 39); NPSVAAAI (SEQ ID NO: 40); PSVAAAI (SEQ ID NO: 41); LNPSVAASI (SEQ ID NO: 42); NPSVAASI (SEQ ID NO: 43); PSVAASI (SEQ ID NO: 44); LNPSVAAWI (SEQ ID NO: 45); NPSVAAWI (SEQ ID NO: 46); GAVPDLAWL (SEQ ID NO: 15); GAVPDLATL (SEQ ID NO: 16) or PSVAAWI (SEQ ID NO: 47).

7. The nucleic acid of claim 1, wherein the amino acid sequence consists of LNPSVAATL (SEQ ID NO: 1); LNPSVAAAL (SEQ ID NO: 30); LNPSVAASL (SEQ ID NO: 33); or LNPSVAAWL (SEQ ID NO: 36).

8. The nucleic acid of claim 1, wherein the amino acid sequence consists of LNPSVAATL (SEQ ID NO: 1).

9. The nucleic acid of claim 1, wherein the amino acid sequence consists of VAPWNAATL (SEQ ID NO: 4).

10. The nucleic acid of claim 1, wherein the amino acid sequence consists of VAPWNSATL (SEQ ID NO: 7).

11. The nucleic acid of claim 1, wherein the amino acid sequence consists of VAPWNAAAL (SEQ ID NO: 13).

12. The nucleic acid of claim 1, wherein the amino acid sequence consists of comprises GAVPDLAWL (SEQ ID NO: 15) or GAVPDLATL (SEQ ID NO: 16).

* * * * *